US009045553B2

(12) United States Patent
Knopf et al.

(10) Patent No.: US 9,045,553 B2
(45) Date of Patent: *Jun. 2, 2015

(54) CERBERUS/COCO DERIVATIVES AND USES THEREOF

(71) Applicant: Acceleron Pharma, Inc., Cambridge, MA (US)

(72) Inventors: John Knopf, Carlisle, MA (US); Jasbir Seehra, Lexington, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/774,585

(22) Filed: Feb. 22, 2013

(65) Prior Publication Data

US 2013/0209462 A1 Aug. 15, 2013

Related U.S. Application Data

(60) Continuation-in-part of application No. 12/940,740, filed on Nov. 5, 2010, which is a division of application No. 12/001,494, filed on Dec. 10, 2007, now Pat. No. 7,833,971, and a continuation-in-part of application No. 13/533,733, filed on Jun. 26, 2012, now abandoned, which is a continuation of application No. 11/597,182, filed as application No. PCT/US2005/018928 on May 27, 2005, now abandoned.

(60) Provisional application No. 60/873,933, filed on Dec. 8, 2006, provisional application No. 60/575,062, filed on May 27, 2004.

(51) Int. Cl.
*C07K 14/00* (2006.01)
*A61K 6/00* (2006.01)
*C07K 14/47* (2006.01)
*C07K 14/52* (2006.01)
*A61K 38/00* (2006.01)

(52) U.S. Cl.
CPC ............. *C07K 14/47* (2013.01); *A61K 38/00* (2013.01); *C07K 14/52* (2013.01); *C07K 2319/01* (2013.01); *C07K 2319/20* (2013.01); *C07K 2319/30* (2013.01); *C07K 2319/31* (2013.01)

(58) Field of Classification Search
CPC .................................. A61K 6/00; C07K 14/00
USPC .............................................. 514/1; 530/350
See application file for complete search history.

(56) References Cited

U.S. PATENT DOCUMENTS

| 5,935,852 | A | 8/1999 | Follettie et al. |
| 6,133,232 | A | 10/2000 | De Robertis et al. |
| 6,610,510 | B1 | 8/2003 | Valenzuela et al. |
| 7,316,998 | B2 * | 1/2008 | Knopf et al. ................ 424/141.1 |
| 7,619,065 | B2 * | 11/2009 | Davies et al. .................. 530/351 |
| 7,833,971 | B2 * | 11/2010 | Grinberg et al. .............. 514/17.7 |
| 7,981,857 | B2 * | 7/2011 | Knopf et al. ....................... 514/1 |
| 2002/0164682 | A1 | 11/2002 | Follettie et al. |
| 2003/0134790 | A1 | 7/2003 | Langenfeld |
| 2003/0194704 | A1 | 10/2003 | Penn et al. |
| 2003/0199042 | A1 | 10/2003 | Valenzuela et al. |
| 2004/0005560 | A1 | 1/2004 | Isogai et al. |
| 2004/0181033 | A1 | 9/2004 | Han et al. |
| 2005/0186663 | A1 | 8/2005 | Davies et al. |
| 2006/0105376 | A1 | 5/2006 | Isogai et al. |
| 2011/0046057 | A1 | 2/2011 | Grinberg et al. |

FOREIGN PATENT DOCUMENTS

| EP | 1347046 A1 | 9/2003 |
| WO | WO-97/48275 | 12/1997 |
| WO | WO-98/34951 | 8/1998 |
| WO | WO-98/49296 | 11/1998 |
| WO | WO-99/01553 | 1/1999 |
| WO | WO-99/40181 | 8/1999 |
| WO | WO-00/55193 | 9/2000 |
| WO | WO 02/10214 | 2/2002 |
| WO | WO-02/32929 | 4/2002 |
| WO | WO-02/054940 | 7/2002 |
| WO | WO-02/077204 | 10/2002 |
| WO | WO-02/078516 | 10/2002 |
| WO | WO-02/090992 | 11/2002 |
| WO | WO-03/012082 | 2/2003 |
| WO | WO-03/055443 | 7/2003 |
| WO | WO-03/055911 | 7/2003 |
| WO | WO-03/072714 | 9/2003 |
| WO | WO-03/106657 A2 | 12/2003 |
| WO | WO-2004/074460 | 9/2004 |
| WO | WO-2005/003158 | 1/2005 |

OTHER PUBLICATIONS

Stanley et al., "Murine cerberus homologue *Cer1* maps to chromosome 4," Genomics 49:337-338 (1998).
Pearce et al., "A mouse cerberus/dan-related gene family," Developmental Biology 209:98-110 (1999).
Marques et al., "The activity of the nodal antagonist *Cerl-2* in the mouse node is required for correct L/R body axis," Genes & Development 18:2342-2347 (2004).
Lah et al., "Human cerberus related gene *CER1* maps to chromosome 9," Genomics 55:364-366 (1999).
Katoh et al., "Identification and characterization of human *CKTSF1B2* and *CKTSF1B3* genes in silico," Oncology Reports 12:423-427 (2004).
Avsian-Kretchmer et al., "Comparative geneomic analysis of the eight-membered ring cystine knot-containing bone morphogenetic protein antagonists," Molecular Endocrinology 18(1):1-12 (2004).

(Continued)

*Primary Examiner* — Karen Cochrane Carlson
(74) *Attorney, Agent, or Firm* — Ropes & Gray LLP

(57) ABSTRACT

The invention relates to Cerberus/Dan/Gremlin polypeptides or variants thereof for use in treating a variety of disorders associated with myostatin, nodal and GDF-11. Preferred polypeptides are Coco or Cerberus derivatives.

14 Claims, 9 Drawing Sheets

(56) References Cited

OTHER PUBLICATIONS

Belo et al., "Cerberus-like is a secreted factor with neuralizing activity expressed in the anterior primitive endoderm of the mouse gastrula," Mechanisms of Development 68:45-57 (1997).

Biben et al., "Murine Cerberus Homologue mCer-1: A canadidate anterior patterning molecule," Developmental Biology 194:135-151 (1998).

Bouwmeester et al., "Cerberus is a head-inducing secreted factor expressed in the anterior endoderm of Spemann's organizer," Nature 382:595-601 (1996).

Piccolo et al., "The head inducer Cerberus is a multifunctional antagonist of Nodal, BMP and Wnt signals," Nature 397:707-710 (1999).

Kuroda et al., "Neural Induction in *Xenopus*: requirement for extodermal and endomesodermal signals via chordin, noggin, β-catenin and cerberus," PLoS Biology 2(5):0623-0634 (2004).

Silva et al., "Endogenous Cerberus activity is required for anterior head specification in *Xenopus*," Development 130(20):4943-4953 (2003).

Esteban et al., "The novel Cer-like protein Caronte mediates the establishment of embryonic left-right asymmetry," Nature 401:243-251 (1999).

Yanagita, M., "BMP antagonists: Their roles in development and involvement in pathophysiology," Cytokine and Growth Factor Reviews, 16(3):309-319 (2005).

Brecher, A.S., et al., "Acetaldehyde Inhibits Chymotrypsin and Serum Anti-Chymotrypsin Activity," J. Investig Med., 46(4):146-152 (1998). Abstract only.

Livingston, S.F., et al., "The Significance of Chymotrypsin-Inhibitor Levels in the Serum of Patients with Carcinoma of the Breast," Cancer Research, 17(9):857-861 (1957).

The Chimpanzee Sequencin and Analysis Consortium. "Initial sequence of the chimpanzee genome and comparison with the human genome," Nature 437:69-87 (2005.

\* cited by examiner

```
   1 CCA CGC GTC CGA GAA AAT TGG AAA CCA GCG ACT CTG GGT CAA TCT TGA CCC TCC AGC CAG ACG ACA
                                                                                   M   L   L
  67 GGG GAC CGA CAA ACC CCC AGA CCC CAA ACC CTA ATA AGG AGG ATT GTG TAA GAA GAC ATG CTG TTG
      F   Q   A   T   S   L   L   A   L   L   C   F   T   V   R   A   F   P   F   M   E   E
 133 TTC CAG GCC ACC AGC CTA TTG GCC CTT CTC TGT TTC ACG GTC AGG GCA TTT CCC TTT ATG GAA GAA
      E   G   S   A   S   F   A   Q   N   V   L   H   S   R   S   F   P   V   S   H   H   G
 199 GAA GGG TCG GCT TCG TTT GCC CAG AAT GTG CTC CAC AGC AGA TCC TTC CCA GTC TCC CAC CAT GGA
      A   F   M   D   L   P   L   F   R   Q   N   R   R   K   I   S   Q   N   F   I   L   H
 265 GCT TTC ATG GAC CTG CCG CTA TTC AGA CAG AAC AGG AGG AAA ATA TCC CAG AAT TTC ATC CTG CAC
      S   D   P   R   E   H   M   D   E   E   A   L   R   R   K   L   V   W   E   S   A   I
 331 TCA GAT CCC AGA GAG CAC ATG GAT GAG GAG GCG CTG AGG AGA AAA CTG GTG TGG GAG AGC GCC ATC
      R   R   D   K   M   R   S   Q   P   D   Q   V   L   P   I   G   Q   D   A   L   K   R
 397 CGC AGG GAC AAG ATG AGA TCC CAA CCA GAC CAG GTG CTG CCC ATT GGG CAA GAT GCT CTG AAA CGC
      S   R   C   H   A   L   P   F   I   Q   N   V   F   R   K   N   C   F   P   V   R   L
 463 TCC AGA TGC CAT GCC TTG CCT TTC ATA CAG AAT GTG TTC AGG AAG AAC TGC TTC CCA GTG CGC CTG
      P   N   K   P   C   F   G   Q   C   N   S   F   Y   V   P   G   W   P   A   G   L   S
 529 CCT AAC AAG TTC TGC TTT GGC CAG TGC AAC TCC TTC TAT GTG CCT GGT TGG CCT GCC GGA CTC TCC
      Q   P   C   T   S   C   A   P   S   R   R   R   I   S   L   P   L   R   C   R   S
 595 CAG CCC TGT ACG TCC TGC GCC CCC AGT CGA CGC CGG CGC ATT TCG CTG CCG TTA CGC TGT CGT TCC
      G   H   L   A   W   Q   E   V   E   L   V   E   E   C   E   C   E   T   R   Y   D   R
 661 GGT CAC CTT GCT TGG CAA GAG GTG GAG CTG GTG GAA GAG TGC GAG TGC GAA ACC CGC TAC GAC AGG
      N   T   V   E   P   A   G   S   E   D   Y   L   P   V   S   *
 727 AAT ACG GTG GAG CCA GCT GGC AGC GGA GAC GAC TAC CTC CCT GTA TCG GCC CAA ACC GCT CTA
 793 CAT GTG CCC AAA TGG ACC AAA CTA TGT GAC CCG GGG CCT TGG CGC TCC CAG TAA CTT CAC CCT TTC
 859 ACA GGC GTC CCT TTG CCA AAG CAG GGG AAG TTC CAA CGA CTT GAC GAC TTT ATT TAA GAA TGA ACA
 925 GTT CTG ACC GAC GGC TGA TTT ATA CGC TTG TCT AGA TTC CCA GAA TCC CTA GGG GGA AAG CCT GTG
 991 ACG AAG CTC CCG CTT TAT TGG GAG GGT GTG AGT AAT GAT TCA ACA TGG CGA AAT TCT GCC TCT TAT
1057 TGT ACC CGG GAG ACT GGT CTC CTG CCA TAT TGT GCT GTG TAT AAG GGC TGT GCC CGT CCT GCT CAT
1123 CTT TTA TAC AAG TGA TGC TTT TAT TGG TAG TTA TTA TGC ATT GTC TGT GCC ACT CCT GTT GTC AAT
1189 TCA ACT TTC CAG ACC GCG TCT ATA AGT GTC ATG GTT ATT GAT CGC GTT GGT TTT GCC TTT CTG CAC
1255 TGC TGC TTC TGA CTC TTA AAA TAA TGT AGG TTC TTC TCC AGG TCA GTT GAT CCG CTG CCT GCT GCA
1321 TTG TTT TGG GAG TCT GAG CCA GCA GTG CAG AGA ATA TAA ACA GAC ATG GCT TCC AAT AGC AGT GAC
1387 TTT TAC CTA GAA CCA GTG GAA ATG AGG AAT GGA TAT TGG AAA GTC TTA TTC CTG ATT TTA AGC A
```

Fig. 3A

```
xCoco     (1)  ALKRSRCHALPFIQNVYRKCSPVRLSRKCSAQCSSYVPGWP--------AGLSQPCTSCPSFSRRISLPUR
mCoco     (1)  ---------------VISRPGCSAEVLSHLCWGRCSSFYIPSSDP--------TPVVPCNSCVPARKRWTSVMLW
hCoco     (1)  ---------------VPSRPGCSAIHLSHLCWGKCSSLYIPGSDP--------TPLVLCNSCMPARKRWARVWLW
fugu Coco (1)  KEGKQSCSCVPPTQRVTAAGCRAVTVHRKICSQQSSLPVPSEAPLGTGMGLLSHRGPCSPCSPSKAHAVVLRIL
xCerberus (1)  EIKSRCRSLPPTQNIVHENCDPSVFQSNLCSGKCSSLPVPNQ--------QDRRNTCSKCLPSKSILMHLTLN
hCerberus (1)  EVENETCRIVPPSQTITHEGCEKVWQSNLCSGKCSSMPGAA--------QHSHTSCSKCLPAKFTSMHLPLN
cCerberus (1)  EVENETCRILPPFNCCAHEDCQKVWQSNLCSGKCSSIRFPCEG--------ADAHSPCSRCSPTKPTRVMLIN
cCaronte  (1)  EWKETCRILPFSQSVAHESCBKVIVQSNLCSGKCSSSFVPGPD--------DRLYTPCSRCLPTKFMKHFTLN xCoco     (68) CRSGHL-----AMQEVELVEECSCSTRYDRNTVEPAGSGEDYLRVS----
mCoco     (54) CSAGQLASPREVRISTVLNQKCQCRPEL---------------
hCoco     (54) CLTGSSASRREVKISTMLIEGCRCSPKA---------------
fugu Coco (76) CSARVQ-----EFRTSERSGDLEHNDDNNDDDDGDGGDGDIDVAG---
xCerberus (67) CTGSKN-----VVKVVMPVEECCRAHKSNPHQTAQFNMDTSTIHH---
hCerberus (68) CTELSS-----VISVVMLVEECQCKVRTEHEIGHILEAGSQDSRIPG---
cCerberus (68) CHSPTP-----VVKMVMQVEECQCMSTERGEERLLLAGSQGSEIPG---
cCaronte  (69) CHSSVP-----VVKKVMLVEECECETQKIEDP--LLGS-LQSDFLGNVPS
```

Fig. 3B

```
                        SEQUENCE LISTING

<160> NUMBER OF SEQ ID NOS: 37

<210> SEQ ID NO 1
<211> LENGTH: 14
<212> TYPE: PRT
<213> ORGANISM: Homo sapiens

<400> SEQUENCE: 1

Pro Pro Gly Thr Gln Ser Leu Ile Gln Pro Ile Asp Gly Met
1               5                   10

<210> SEQ ID NO 2
<211> LENGTH: 27
<212> TYPE: PRT
<213> ORGANISM: Homo sapiens

<400> SEQUENCE: 2

Cys Lys Val Lys Thr Glu His Glu Asp Gly His Ile Leu His Ala Gly
1               5                   10                  15

Ser Gln Asp Ser Phe Ile Pro Gly Val Ser Ala
            20                  25

<210> SEQ ID NO 3
<211> LENGTH: 189
<212> TYPE: PRT
<213> ORGANISM: Homo sapiens

<400> SEQUENCE: 3

Met Leu Leu Gly Gln Leu Ser Thr Leu Leu Cys Leu Leu Ser Gly Ala
1               5                   10                  15

Leu Pro Thr Gly Ser Gly Arg Pro Glu Pro Gln Ser Pro Arg Pro Gln
            20                  25                  30

Ser Trp Ala Ala Ala Asn Gln Thr Trp Ala Leu Gly Pro Gly Ala Leu
        35                  40                  45

Pro Pro Leu Val Pro Ala Ser Ala Leu Gly Ser Trp Lys Ala Phe Leu
    50                  55                  60

Gly Leu Gln Lys Ala Arg Gln Leu Gly Met Gly Arg Leu Gln Arg Gly
65                  70                  75                  80

Gln Asp Glu Val Ala Ala Val Thr Leu Pro Leu Asn Pro Gln Glu Val
                85                  90                  95

Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
        115                 120                 125

Cys Ser Ser Leu Tyr Ile Pro Gly Ser Asp Pro Thr Pro Leu Val Leu
    130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Val Lys Ile Ser
                165                 170                 175

Thr Met Leu Ile Glu Gly Cys His Cys Ser Pro Lys Ala
            180                 185

<210> SEQ ID NO 4
```

```
<211> LENGTH: 272
<212> TYPE: PRT
<213> ORGANISM: Mus musculus

<400> SEQUENCE: 4

Met His Leu Leu Leu Val Gln Leu Val Leu Leu Pro Leu Gly Lys
1               5                   10                  15

Ala Asp Leu Cys Val Asp Gly Cys Gln Ser Gln Gly Ser Leu Ser Phe
            20                  25                  30

Pro Leu Leu Glu Arg Gly Arg Arg Asp Leu His Val Ala Asn His Glu
            35                  40                  45

Glu Ala Glu Asp Lys Pro Asp Leu Phe Val Ala Val Pro His Leu Met
    50                  55                  60

Gly Thr Ser Leu Ala Gly Glu Gly Gln Arg Gln Arg Gly Lys Met Leu
65                  70                  75                  80

Ser Arg Leu Gly Arg Phe Trp Lys Lys Pro Glu Thr Glu Phe Tyr Pro
                85                  90                  95

Pro Arg Asp Val Glu Ser Asp His Val Ser Ser Gly Met Gln Ala Val
            100                 105                 110

Thr Gln Pro Ala Asp Gly Arg Lys Val Glu Arg Ser Pro Leu Gln Glu
            115                 120                 125

Glu Ala Lys Arg Phe Trp His Arg Phe Met Phe Arg Lys Gly Pro Ala
130                 135                 140

Phe Gln Gly Val Ile Leu Pro Ile Lys Ser His Glu Val His Trp Glu
145                 150                 155                 160

Thr Cys Arg Thr Val Pro Phe Asn Gln Thr Ile Ala His Glu Asp Cys
                165                 170                 175

Gln Lys Val Val Val Gln Asn Asn Leu Cys Phe Gly Lys Cys Ser Ser
            180                 185                 190

Ile Arg Phe Pro Gly Glu Gly Ala Asp Ala His Ser Phe Cys Ser His
        195                 200                 205

Cys Ser Pro Thr Lys Phe Thr Thr Val His Leu Met Leu Asn Cys Thr
    210                 215                 220

Ser Pro Thr Pro Val Val Lys Met Val Met Gln Val Glu Glu Cys Gln
225                 230                 235                 240

Cys Met Val Lys Thr Glu Arg Gly Glu Glu Arg Leu Leu Ala Gly
                245                 250                 255

Ser Gln Gly Ser Phe Ile Pro Gly Leu Pro Ala Ser Lys Thr Asn Pro
            260                 265                 270

<210> SEQ ID NO 5
<211> LENGTH: 267
<212> TYPE: PRT
<213> ORGANISM: Homo sapiens

<400> SEQUENCE: 5

Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
            35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80
```

Ser Arg Phe Gly Arg Phe Trp Lys Lys Pro Glu Arg Glu Met His Pro
            85                  90                  95

Ser Arg Asp Ser Asp Ser Glu Pro Phe Pro Gly Thr Gln Ser Leu
100                 105                 110

Ile Gln Pro Ile Asp Gly Met Lys Met Glu Lys Ser Pro Leu Arg Glu
            115                 120                 125

Glu Ala Lys Lys Phe Trp His His Phe Met Phe Arg Lys Thr Pro Ala
130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
            165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
            195                 200                 205

Cys Leu Pro Ala Lys Phe Thr Thr Met His Leu Pro Leu Asn Cys Thr
210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
            245                 250                 255

Ser Gln Asp Ser Phe Ile Pro Gly Val Ser Ala
            260                 265

<210> SEQ ID NO 6
<211> LENGTH: 804
<212> TYPE: DNA
<213> ORGANISM: Homo sapiens

<400> SEQUENCE: 6
atgcatctcc tcttatttca gctgctggta ctcctgcctc taggaaagac cacacggcac      60
caggatggcc gccagaatca gagttctctt tcccccgtac tcctgccaag gaatcaaaga     120
gagcttccca caggcaacca tgaggaagct gaggagaagc cagatctgtt tgtcgcagtg     180
ccacaccttg tagccaccag ccctgcaggg aaggccagag gcagagaga aagatgctg       240 tccagatttg gcaggttctg gaagaagcct gagagagaaa tgcatccatc cagggactca     300
gatagtgagc ccttcccacc tgggacccag tccctcatcc agccgataga tggaatgaaa     360
atggagaaat ctcctcttcg ggaagaagcc aagaaattct ggcaccactt catgttcaga     420
aaaactccgg cttctcaggg ggtcatcttg cccatcaaaa gccatgaagt acattgggag     480
acctgcagga cagtgccctt cagccagact ataacccacg aaggctgtga aaaagtagtt     540
gttcagaaca accttttgct tgggaaatgc gggtctgttc attttcctgg agccgcgcag     600
cactcccata cctcctgctc tcactgtttg cctgccaagt tcaccacgat gcacttgcca     660
ctgaactgca ctgaactttc ctccgtgatc aaggtggtga tgctggtgga ggagtgccag     720
tgcaaggtga agacggagca tgaagatgga cacatcctac atgctggctc ccaggattcc     780
tttatcccag gagtttcagc ttga                                            804

<210> SEQ ID NO 7
<211> LENGTH: 1752
<212> TYPE: DNA
<213> ORGANISM: Mus musculus
<220> FEATURE:

<221> NAME/KEY: modified_base
<222> LOCATION: (1235)..(1235)
<223> OTHER INFORMATION: a, c, t or g
<220> FEATURE:
<221> NAME/KEY: modified_base
<222> LOCATION: (1313)..(1313)
<223> OTHER INFORMATION: a, c, t or g

<400> SEQUENCE: 7

```
gggggggggg ggggtcagag ggagctttct tttaggcccg tccatctgtg aatctaacct      60
cagtttctgg gaatcaggaa gcatgcatct cctcttagtt cagctgcttg ttctcttgcc     120
tctggggaag gcagacctat gtgtggatgg ctgccagagt cagggctctt tatcctttcc     180
tctcctagaa aggggtcgca gagatctcca cgtggccaac cacgaggagg cagaagacaa     240
gccggatctg tttgtggccg tgccacacct catgggcacc agcctggctg ggaaggcca      300
gaggcagaga gggaagatgc tgtccaggct tggaagattc tggaagaaac ctgagaccga     360
attttacccc ccaagggatg tggaaagcga tcatgtctca tcggggatgc aggccgtgac     420
tcagccagca gatgggagga aagtggagag atcacctcta caggaggaag ccaagaggtt     480
ctggcatcgg ttcatgttca gaaagggccc ggcgttccag ggagtcatcc tgcccatcaa     540
aagccacgaa gtacactggg agacctgcag gactgtgccc ttcaaccaga ccattgccca     600
tgaagactgt caaaaagtcg ttgtccagaa caacctttgc tttggcaaat gcagttccat     660
tcgttttccc ggagaagggg cagatgccca cagcttctgc tcccactgct cgcccaccaa     720
attcaccacc gtgcacttga tgctgaactg caccagccca accccgtgg tcaagatggt      780
gatgcaagta gaagagtgtc agtgcatggt gaagacggaa cgtggagagg agcgcctcct     840
actggctggt tcccagggtt ccttcatccc tggacttcca gcttcaaaaa caaacccatg     900
aattacctca acagaaagca aaacctcaac agaataagtg agggttattc aatctggaaa     960
tgttatgtga gttatataaa gatcagtgga aaatatcttt ctctctccct ctctcccct    1020
ctctcttctc tctattttct ctctctctct ctctctctct ctctctctct ctctctctca    1080
cacacacaca cacacacaca cacacacaca catgtttgtg tttagacagg gtcttatgta    1140
ttctcagctg gcctcaaact cacaatgtgg ctgggatga ttttaaactc ctgatccaat     1200
tcctgagtgc tgggattaca gacatgctcc ataanacata gctcccagaa ggatttttaa    1260
aagagatttt gcatgtttca aagttgcctt tgagactcag aaatattttg atntattgaa    1320
tggccttgcc acagatgtgg gaggcagctt gcttggtggc ccaagtattt ttttttgtt     1380
cgttcagaat tctccacatg aagttttac tgttggttat ctggcgttga agaaggaata     1440
gtgaaggtac ttttaacagt ttacacgtgg aaggggctca ggcactagga accaaccttt    1500
tcccggaata tgaggaaaat acatgaacag tattagagtc acttgaggaa gttactagga    1560
aacgccataa gtctccaagt acattgtgag tcattttgaa ggacaatcgt gtatatagac    1620
gaaatcttct actcgtatgc ttttgaatct tctagcaagt taggtttcta tgtttgggct    1680
tcttcctatt gtctaagagt atgtgtgaca aattcaacct gacaaatacc tcaatggcaa    1740
attctgaccc tg                                                        1752
```

<210> SEQ ID NO 8
<211> LENGTH: 1731
<212> TYPE: DNA
<213> ORGANISM: Homo sapiens

<400> SEQUENCE: 8

```
agtccggaca gacagacagg cagacagacg cacggacaag cagatgctcc ttggccagct      60
```

```
atccactctt ctgtgcctgc ttagcggggc cctgcctaca ggctcaggga ggcctgaacc      120
ccagtctcct cgacctcagt cctgggctgc agccaatcag acctgggctc tgggcccagg      180
ggccctgccc ccactggtgc cagcttctgc ccttgggagc tggaaggcct tcttgggcct      240
gcagaaagcc aggcagctgg ggatgggcag gctgcagcgt gggcaagacg aggtggctgc      300
tgtgactctg ccgctgaacc ctcaggaagt gatccagggg atgtgtaagg ctgtgccctt      360
cgttcaggtg ttctcccggc ccggctgctc agccatacgc ctccgaaatc atctgtgctt      420
tggtcattgc tcctctctct acatccctgg ctcggacccc accccactag tcctgtgcaa      480
cagctgtatg cctgctcgca agcgttgggc accgtggtc ctgtggtgtc tcactggcag       540
ctcagcctcc cgtcgacggg tgaagatatc caccatgctg atcgaggggt gtcactgcag      600
cccaaaagca tgaactgagc atcgtggatg ggtgcacgga cacacgcacc ttggagaaat      660 gagggggagat ggaccaagaa agacgtggac ctggatgatg tactctgggt caagagacca     720
gggatgcagg gttaggcaga caggtcccca gagtcctcac cctgctcccc agacagtaga      780
cacagtgccc gtcctggagt tgcaccactg atagtcacag cacacaatga ttgacaactc      840 acttttttt ttttttttga gatggagtct cgctctgtcg cccaggctgg agtgcagtgg       900
cgcaatctca gctcactgca agctccacct cccgggttta tgccattctc ctgtctcagc      960
ctcccgagta gctgggacta caggcacccg ccaacacgcc cggctaattt ttcgtatttt     1020
tagtaaagac agggtttcac cgtgttagcc aggatggtct ctatctcctg acctcgtgat     1080
ctgcctgcct tggccttatt attttttttt tttaaggaca gagtctctct ctgtcaccca     1140
ggctggagtg caatggcgcg atcttggctc actgtaactt ccacttgcca ggctcaagca     1200
gttctcctgc ctcagcctcc tgagtagctg ggactacagg cacccgccac catgcccagc     1260 taattttttgt attttttagta gagacagagt ttcaccatat tagcctggct ggtctcaaac    1320
tcctggcctc aggtgatctg cccacctcgg cctcccaaag tgctgggatc aaatccactg     1380
ttaatcatta ggctgaactg tctcttatag aatgaggtca agacactcc cagttgcagg      1440 gagggtagat ggccccaccc agaccgagag acacagtgat gacctcagcc tagggacacc     1500
aaaaaaaaaa aaaaaaaaa cccaaaccaa aaacgcaaac caaagcaggc aggcagacag      1560
ctgctggggg aaatcctggg gtccttgaga cagaggcagg accctcgtgt cccagctgc     1620 ctcttgcctt gatagtggtg ctgtgtccct ctcagacccc ccacctgagt ctccacagag     1680
ccccacgcct ggcatggcat tccacagaaa ccataaaggt tggctgagtc c              1731
```

<210> SEQ ID NO 9
<211> LENGTH: 75
<212> TYPE: PRT
<213> ORGANISM: Homo sapiens

<400> SEQUENCE: 9

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro
65                  70                  75

-continued

<210> SEQ ID NO 10
<211> LENGTH: 70
<212> TYPE: PRT
<213> ORGANISM: Homo sapiens

<400> SEQUENCE: 10

Ala Leu Leu Cys Ala Cys Thr Ser Cys Leu Gln Ala Asn Tyr Thr Cys
1               5                   10                  15

Glu Thr Asp Gly Ala Cys Met Val Ser Ile Phe Asn Leu Asp Gly Met
            20                  25                  30

Glu His His Val Arg Thr Cys Ile Pro Lys Val Glu Leu Val Pro Ala
        35                  40                  45

Gly Lys Pro Phe Tyr Cys Leu Ser Ser Glu Asp Leu Arg Asn Thr His
    50                  55                  60

Cys Cys Tyr Thr Asp Tyr
65                  70

<210> SEQ ID NO 11
<211> LENGTH: 1450
<212> TYPE: DNA
<213> ORGANISM: Xenopus laevis

<400> SEQUENCE: 11
ccacgcgtcc gagaaaattg gaaaccagcg actctgggtc aatcttgacc ctccagccag      60
acgacagggg accgacaaac ccccagaccc caaaccctaa taaggaggat tgtgtaagaa     120
gacatgctgt tgttccaggc caccagccta ttggcccttc tctgtttcac ggtcagggca     180
tttcccttta tggaagaaga agggtcggct tcgtttgccc agaatgtgct ccacagcaga     240
tccttcccag tctcccacca tggagctttc atggacctgc cgctattcag acagaacagg     300
aggaaaatat cccagaattt catcctgcac tcagatccca gagagcacat ggatgaggag     360
gcgctgagga gaaaactggt gtgggagagc gccatccgca gggacaagat gagatcccaa     420
ccagaccagg tgctgcccat gggcaagat gctctgaaac gctccagatg ccatgccttg     480
cctttcatac agaatgtgtt caggaagaac tgcttcccag tgcgcctccc taacaagttc     540
tgctttggcc agtgcaactc cttctatgtg cctggttggc ctgccggact ctcccagccc     600
tgtacgtcct cgcgccccag tcgatcccgg cgcatttcgc tgccgttacg ctgtcgttcc     660
ggtcaccttg cttggcaaga ggtggagctg gtggaagagt gcgagtgcga aacccgctac     720
gacaggaata cggtggagcc agctggcagc ggagaggact acctgcccgt tcataggcc      780
caaaccgctc tacatgtgcc caaatggacc aaactatgtg accggggcc ttggcgctcc      840
cagtaacttc accctttgac aggcgtccct ttgccaaagc aggggaagtt ccaacgactt     900
gacgactta tttaagaatg aacagttctg accgacggct gatttatacg cttgtctaga     960
ttcccagaat ccctaggggg aaagcctgtg acgaagctcc cgctttattg ggagggtgtg    1020
agtaatgatt caacatggcg gaattctgcc tcttattgta cccgggagac tggtctcgtg    1080
ccatattgtg ctgtgtataa gggctgtgcc cgtcctgctc atcttttata caagtgatgc    1140
ttttattggt agttattatg cattgtctgt gccagtcctg ttgtcaattc aactttccag    1200
accgcgtcta aagtgtcat ggttattgat ggcgttggtt ttgccttct gcactgctgg     1260
ttctgactct taaaataatg taggttcttg tccaggtcag ttgatccgct ggctgctgca    1320
ttgttttggg agtctgagcc agcagtgcag agaatataaa cagacatggc ttccaatagc    1380
agtgactttt acctagaacc agtggaaatg aggaatggat attgggaagt cttattcctg    1440
attttaagca                                                      1450

<210> SEQ ID NO 12
<211> LENGTH: 217
<212> TYPE: PRT
<213> ORGANISM: Xenopus laevis

<400> SEQUENCE: 12

Met Leu Leu Phe Gln Ala Thr Ser Leu Leu Ala Leu Leu Cys Phe Thr
1               5                   10                  15

Val Arg Ala Phe Pro Phe Met Glu Glu Glu Gly Ser Ala Ser Phe Ala
            20                  25                  30

Gln Asn Val Leu His Ser Arg Ser Phe Pro Val Ser His His Gly Ala
        35                  40                  45

Phe Met Asp Leu Pro Leu Phe Arg Gln Asn Arg Arg Lys Ile Ser Gln
    50                  55                  60

Asn Phe Ile Leu His Ser Asp Pro Arg Glu His Met Asp Glu Glu Ala
65                  70                  75                  80

Leu Arg Arg Lys Leu Val Trp Glu Ser Ala Ile Arg Arg Asp Lys Met
                85                  90                  95

Arg Ser Gln Pro Asp Gln Val Leu Pro Ile Gly Gln Asp Ala Leu Lys
            100                 105                 110

Arg Ser Arg Cys His Ala Leu Pro Phe Ile Gln Asn Val Phe Arg Lys
        115                 120                 125

Asn Cys Phe Pro Val Arg Leu Pro Asn Lys Phe Cys Phe Gly Gln Cys
    130                 135                 140

Asn Ser Phe Tyr Val Pro Gly Trp Pro Ala Gly Leu Ser Gln Pro Cys
145                 150                 155                 160

Thr Ser Cys Ala Pro Ser Arg Ser Arg Ile Ser Leu Pro Leu Arg
                165                 170                 175

Cys Arg Ser Gly His Leu Ala Trp Gln Glu Val Glu Leu Val Glu Glu
            180                 185                 190

Cys Glu Cys Glu Thr Arg Tyr Asp Arg Asn Thr Val Glu Pro Ala Gly
        195                 200                 205

Ser Gly Glu Asp Tyr Leu Pro Val Ser
    210                 215

<210> SEQ ID NO 13
<211> LENGTH: 108
<212> TYPE: PRT
<213> ORGANISM: Xenopus laevis

<400> SEQUENCE: 13

Ala Leu Lys Arg Ser Arg Cys His Ala Leu Pro Phe Ile Gln Asn Val
1               5                   10                  15

Phe Arg Lys Asn Cys Phe Pro Val Arg Leu Pro Asn Lys Phe Cys Phe
            20                  25                  30

Gly Gln Cys Asn Ser Phe Tyr Val Pro Gly Trp Pro Ala Gly Leu Ser
        35                  40                  45

Gln Pro Cys Thr Ser Cys Ala Pro Ser Arg Ser Arg Ile Ser Leu
    50                  55                  60

Pro Leu Arg Cys Arg Ser Gly His Leu Ala Trp Gln Glu Val Glu Leu
65                  70                  75                  80

Val Glu Glu Cys Glu Cys Glu Thr Arg Tyr Asp Arg Asn Thr Val Glu
                85                  90                  95

```
Pro Ala Gly Ser Gly Glu Asp Tyr Leu Pro Val Ser
            100                 105

<210> SEQ ID NO 14
<211> LENGTH: 81
<212> TYPE: PRT
<213> ORGANISM: Mus musculus

<400> SEQUENCE: 14

Val Ile Ser Arg Pro Gly Cys Thr Ser Ala Arg Val Leu Asn His Leu
1               5                   10                  15

Cys Phe Gly Arg Cys Ser Ser Phe Tyr Ile Pro Ser Ser Asp Pro Thr
            20                  25                  30

Pro Val Val Phe Cys Asn Ser Cys Val Pro Ala Arg Lys Arg Trp Thr
        35                  40                  45

Ser Val Thr Leu Trp Cys Gly Ala Gly Gln Leu Ala Ser Pro Arg Arg
    50                  55                  60

Val Arg Ile Ser Thr Val Leu Val Gln Lys Cys Gln Cys Arg Pro Lys
65                  70                  75                  80

Leu

<210> SEQ ID NO 15
<211> LENGTH: 81
<212> TYPE: PRT
<213> ORGANISM: Homo sapiens

<400> SEQUENCE: 15

Val Phe Ser Arg Pro Gly Cys Ser Ala Ile Arg Leu Arg Asn His Leu
1               5                   10                  15

Cys Phe Gly His Cys Ser Ser Leu Tyr Ile Pro Gly Ser Asp Pro Thr
            20                  25                  30

Pro Leu Val Leu Cys Asn Ser Cys Met Pro Ala Arg Lys Arg Trp Ala
        35                  40                  45

Pro Val Val Leu Trp Cys Leu Thr Gly Ser Ser Ala Ser Arg Arg Arg
    50                  55                  60

Val Lys Ile Ser Thr Met Leu Ile Glu Gly Cys His Cys Ser Pro Lys
65                  70                  75                  80

Ala

<210> SEQ ID NO 16
<211> LENGTH: 117
<212> TYPE: PRT
<213> ORGANISM: Fugu rubripes

<400> SEQUENCE: 16

Lys Glu Gly Lys Gln Ser Cys Ser Gly Val Pro Phe Thr Gln Arg Val
1               5                   10                  15

Thr Ala Ala Gly Cys Ser Ala Val Thr Val His Asn Lys Leu Cys Phe
            20                  25                  30

Gly Gln Cys Ser Ser Leu Phe Val Pro Ser Glu Ala Pro Leu Gly Thr
        35                  40                  45

Gly Met Gly Leu Leu His His Arg Gly Pro Cys Ser Arg Cys Ala Pro
    50                  55                  60

Ser Lys Ala His Ala Val Val Leu Pro Leu Leu Cys Gly Ala Arg Val
65                  70                  75                  80

Gln Glu Lys Arg Thr Ser Glu Arg Ser Arg Gly Asp Leu Glu His Asn
                85                  90                  95
```

```
Asp Asp Asn Asn Asp Asp Asp Gly Asp Gly Gly Gly Asp Gly Asp
                100                 105                 110

Asp Asp Val Ala Gly
            115

<210> SEQ ID NO 17
<211> LENGTH: 108
<212> TYPE: PRT
<213> ORGANISM: Xenopus laevis

<400> SEQUENCE: 17

Glu Ile Met Lys Glu Ala Cys Lys Thr Leu Pro Phe Thr Gln Asn Ile
1               5                   10                  15

Val His Glu Asn Cys Asp Arg Met Val Ile Gln Asn Asn Leu Cys Phe
            20                  25                  30

Gly Lys Cys Ile Ser Leu His Val Pro Asn Gln Gln Asp Arg Arg Asn
        35                  40                  45

Thr Cys Ser His Cys Leu Pro Ser Lys Phe Thr Leu Asn His Leu Thr
    50                  55                  60

Leu Asn Cys Thr Gly Ser Lys Asn Val Val Lys Val Val Met Met Val
65                  70                  75                  80

Glu Glu Cys Thr Cys Glu Ala His Lys Ser Asn Phe His Gln Thr Ala
                85                  90                  95

Gln Phe Asn Met Asp Thr Ser Thr Thr Leu His His
            100                 105

<210> SEQ ID NO 18
<211> LENGTH: 109
<212> TYPE: PRT
<213> ORGANISM: Homo sapiens

<400> SEQUENCE: 18

Glu Val His Trp Glu Thr Cys Arg Thr Val Pro Phe Ser Gln Thr Ile
1               5                   10                  15

Thr His Glu Gly Cys Glu Lys Val Val Val Gln Asn Asn Leu Cys Phe
            20                  25                  30

Gly Lys Cys Gly Ser Val His Phe Pro Gly Ala Ala Gln His Ser His
        35                  40                  45

Thr Ser Cys Ser His Cys Leu Pro Ala Lys Phe Thr Thr Met His Leu
    50                  55                  60

Pro Leu Asn Cys Thr Glu Leu Ser Ser Val Ile Lys Val Val Met Leu
65                  70                  75                  80

Val Glu Glu Cys Gln Cys Lys Val Lys Thr Glu His Glu Asp Gly His
                85                  90                  95

Ile Leu His Ala Gly Ser Gln Asp Ser Phe Ile Pro Gly
            100                 105

<210> SEQ ID NO 19
<211> LENGTH: 109
<212> TYPE: PRT
<213> ORGANISM: Gallus gallus

<400> SEQUENCE: 19

Glu Val His Trp Glu Thr Cys Arg Thr Val Pro Phe Asn Gln Thr Ile
1               5                   10                  15

Ala His Glu Asp Cys Gln Lys Val Val Val Gln Asn Asn Leu Cys Phe
            20                  25                  30

Gly Lys Cys Ser Ser Ile Arg Phe Pro Gly Glu Gly Ala Asp Ala His
```

35                  40                  45

Ser Phe Cys Ser His Cys Ser Pro Thr Lys Phe Thr Thr Val His Leu
 50                  55                  60

Met Leu Asn Cys Thr Ser Pro Thr Pro Val Val Lys Met Val Met Gln
 65                  70                  75                  80

Val Glu Glu Cys Gln Cys Met Val Lys Thr Glu Arg Gly Glu Glu Arg
                 85                  90                  95

Leu Leu Leu Ala Gly Ser Gln Gly Ser Phe Ile Pro Gly
            100                 105

<210> SEQ ID NO 20
<211> LENGTH: 109
<212> TYPE: PRT
<213> ORGANISM: Gallus gallus

<400> SEQUENCE: 20

Glu Met His Gln Glu Thr Cys Arg Thr Leu Pro Phe Ser Gln Ser Val
 1               5                  10                  15

Ala His Glu Ser Cys Glu Lys Val Ile Val Gln Asn Asn Leu Cys Phe
                 20                  25                  30

Gly Lys Cys Ser Ser Phe His Val Pro Gly Pro Asp Asp Arg Leu Tyr
             35                  40                  45

Thr Phe Cys Ser Lys Cys Leu Pro Thr Lys Phe Ser Met Lys His Phe
 50                  55                  60

Asp Leu Asn Cys Thr Ser Ser Val Pro Val Val Lys Lys Val Met Ile
 65                  70                  75                  80

Val Glu Glu Cys Asn Cys Glu Thr Gln Lys Ile Glu Asp Pro Leu Leu
                 85                  90                  95

Gly Ser Leu Gln Ser Asp Phe Leu Gly Asn Val Pro Glu
            100                 105

<210> SEQ ID NO 21
<211> LENGTH: 108
<212> TYPE: DNA
<213> ORGANISM: Artificial Sequence
<220> FEATURE:
<223> OTHER INFORMATION: Description of Artificial Sequence: Synthetic
      CAGA12 polynucleotide motif from PAI-1 gene

<400> SEQUENCE: 21
agccagacaa gccagacaag ccagacaagc cagacaagcc agacaagcca gacaagccag      60
acaagccaga caagccagac aagccagaca agccagacaa gccagaca                 108

<210> SEQ ID NO 22
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Leu Leu Gly Gln Leu Ser Thr Leu Leu Cys Leu Leu Ser Gly Ala
 1               5                  10                  15

Leu Pro Thr Gly Ser Gly Arg Pro Glu Pro Gln Ser Pro Arg Pro Gln
                 20                  25                  30

Ser Trp Ala Ala Ala Asn Gln Thr Trp Ala Leu Gly Pro Gly Ala Leu
             35                  40                  45

Pro Pro Leu Val Pro Ala Ser Ala Leu Gly Ser Trp Lys Ala Phe Leu

```
            50                  55                  60
Gly Leu Gln Lys Ala Arg Gln Leu Gly Met Gly Arg Leu Gln Arg Gly
 65                  70                  75                  80

Gln Asp Glu Val Ala Ala Val Thr Leu Pro Leu Asn Pro Gln Glu Val
                 85                  90                  95

Ile Gln Gly Met Cys Lys Ala Val Pro Phe Val Gln Val Phe Ser Arg
            100                 105                 110

Pro Gly Cys Ser Ala Ile Arg Leu Arg Asn His Leu Cys Phe Gly His
        115                 120                 125

Cys Ser Ser Leu Tyr Ile Pro Gly Ser Asp Pro Thr Pro Leu Val Leu
    130                 135                 140

Cys Asn Ser Cys Met Pro Ala Arg Lys Arg Trp Ala Pro Val Val Leu
145                 150                 155                 160

Trp Cys Leu Thr Gly Ser Ser Ala Ser Arg Arg Val Lys Ile Ser
                165                 170                 175

Thr Met Leu Ile Glu Gly Cys His Cys Ser Pro Lys Ala Thr Gly Gly
            180                 185                 190

Gly Thr His Thr Cys Pro Pro Cys Pro Ala Pro Glu Leu Leu Gly Gly
        195                 200                 205

Pro Ser Val Phe Leu Phe Pro Pro Lys Pro Lys Asp Thr Leu Met Ile
    210                 215                 220

Ser Arg Thr Pro Glu Val Thr Cys Val Val Val Asp Val Ser His Glu
225                 230                 235                 240

Asp Pro Glu Val Lys Phe Asn Trp Tyr Val Asp Gly Val Glu Val His
                245                 250                 255

Asn Ala Lys Thr Lys Pro Arg Glu Glu Gln Tyr Asn Ser Thr Tyr Arg
            260                 265                 270

Val Val Ser Val Leu Thr Val Leu His Gln Asp Trp Leu Asn Gly Lys
        275                 280                 285

Glu Tyr Lys Cys Lys Val Ser Asn Lys Ala Leu Pro Val Pro Ile Glu
    290                 295                 300

Lys Thr Ile Ser Lys Ala Lys Gly Gln Pro Arg Glu Pro Gln Val Tyr
305                 310                 315                 320

Thr Leu Pro Pro Ser Arg Glu Glu Met Thr Lys Asn Gln Val Ser Leu
                325                 330                 335

Thr Cys Leu Val Lys Gly Phe Tyr Pro Ser Asp Ile Ala Val Glu Trp
            340                 345                 350

Glu Ser Asn Gly Gln Pro Glu Asn Asn Tyr Lys Thr Thr Pro Pro Val
        355                 360                 365

Leu Asp Ser Asp Gly Ser Phe Phe Leu Tyr Ser Lys Leu Thr Val Asp
    370                 375                 380

Lys Ser Arg Trp Gln Gln Gly Asn Val Phe Ser Cys Ser Val Met His
385                 390                 395                 400

Glu Ala Leu His Asn His Tyr Thr Gln Lys Ser Leu Ser Leu Ser Pro
                405                 410                 415

Gly Lys

<210> SEQ ID NO 23
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 23

Leu Asn Pro Gln Glu Val Ile Gln Gly Met Cys Lys Ala Val Pro Phe
1               5                   10                  15

Val Gln Val Phe Ser Arg Pro Gly Cys Ser Ala Ile Arg Leu Arg Asn
            20                  25                  30

His Leu Cys Phe Gly His Cys Ser Ser Leu Tyr Ile Pro Gly Ser Asp
        35                  40                  45

Pro Thr Pro Leu Val Leu Cys Asn Ser Cys Met Pro Ala Arg Lys Arg
    50                  55                  60

Trp Ala Pro Val Val Leu Trp Cys Leu Thr Gly Ser Ser Ala Ser Arg
65                  70                  75                  80

Arg Arg Val Lys Ile Ser Thr Met Leu Ile Glu Gly Cys His Cys Ser
                85                  90                  95

Pro Lys Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Val Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 24
<211> LENGTH: 21
<212> TYPE: PRT
<213> ORGANISM: Apis sp.

<400> SEQUENCE: 24

Met Lys Phe Leu Val Asn Val Ala Leu Val Phe Met Val Val Tyr Ile
1               5                   10                  15

Ser Tyr Ile Tyr Ala
            20
```

<210> SEQ ID NO 25
<211> LENGTH: 22
<212> TYPE: PRT
<213> ORGANISM: Unknown
<220> FEATURE:
<223> OTHER INFORMATION: Description of Unknown: Tissue
      plasminogen activator peptide

<400> SEQUENCE: 25

Met Asp Ala Met Lys Arg Gly Leu Cys Cys Val Leu Leu Leu Cys Gly
1               5                   10                  15

Ala Val Phe Val Ser Pro
            20

<210> SEQ ID NO 26
<211> LENGTH: 21
<212> TYPE: PRT
<213> ORGANISM: Homo sapiens

<400> SEQUENCE: 26

Met Leu Leu Gly Gln Leu Ser Thr Leu Cys Leu Leu Ser Gly Ala
1               5                   10                  15

Leu Pro Thr Gly Ser
            20

<210> SEQ ID NO 27
<211> LENGTH: 4
<212> TYPE: PRT
<213> ORGANISM: Homo sapiens

<400> SEQUENCE: 27

Thr Gly Gly Gly
1

<210> SEQ ID NO 28
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
                20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
                100                 105                 110

Ile Gln Pro Ile Asp Gly Met Lys Met Glu Lys Ser Pro Leu Arg Glu
            115                 120                 125

Glu Ala Lys Lys Phe Trp His His Phe Met Phe Arg Lys Thr Pro Ala
        130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
    210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala Thr Gly Gly Gly Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Val Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 29
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val His Trp Glu Thr Cys Arg Thr Val Pro Phe Ser Gln Thr Ile

```
                1               5                   10                  15
            Thr His Glu Gly Cys Glu Lys Val Val Gln Asn Asn Leu Cys Phe
                            20                  25                  30

Gly Lys Cys Gly Ser Val His Phe Pro Gly Ala Ala Gln His Ser His
                            35                  40                  45

Thr Ser Cys Ser His Cys Leu Pro Ala Lys Phe Thr Thr Met His Leu
                            50                  55                  60

Pro Leu Asn Cys Thr Glu Leu Ser Ser Val Ile Lys Val Val Met Leu
            65                  70                  75                  80

Val Glu Glu Cys Gln Cys Lys Val Lys Thr Glu His Glu Asp Gly His
                            85                  90                  95

Ile Leu His Ala Gly Ser Gln Asp Ser Phe Ile Pro Gly Val Ser Ala
                            100                 105                 110

Thr Gly Gly Gly Thr His Thr Cys Pro Pro Cys Pro Ala Pro Glu Leu
                            115                 120                 125

Leu Gly Gly Pro Ser Val Phe Leu Phe Pro Pro Lys Pro Lys Asp Thr
                            130                 135                 140

Leu Met Ile Ser Arg Thr Pro Glu Val Thr Cys Val Val Val Asp Val
            145                 150                 155                 160

Ser His Glu Asp Pro Glu Val Lys Phe Asn Trp Tyr Val Asp Gly Val
                            165                 170                 175

Glu Val His Asn Ala Lys Thr Lys Pro Arg Glu Glu Gln Tyr Asn Ser
                            180                 185                 190

Thr Tyr Arg Val Val Ser Val Leu Thr Val Leu His Gln Asp Trp Leu
                            195                 200                 205

Asn Gly Lys Glu Tyr Lys Cys Lys Val Ser Asn Lys Ala Leu Pro Val
                            210                 215                 220

Pro Ile Glu Lys Thr Ile Ser Lys Ala Lys Gly Gln Pro Arg Glu Pro
            225                 230                 235                 240

Gln Val Tyr Thr Leu Pro Pro Ser Arg Glu Glu Met Thr Lys Asn Gln
                            245                 250                 255

Val Ser Leu Thr Cys Leu Val Lys Gly Phe Tyr Pro Ser Asp Ile Ala
                            260                 265                 270

Val Glu Trp Glu Ser Asn Gly Gln Pro Glu Asn Asn Tyr Lys Thr Thr
                            275                 280                 285

Pro Pro Val Leu Asp Ser Asp Gly Ser Phe Phe Leu Tyr Ser Lys Leu
                            290                 295                 300

Thr Val Asp Lys Ser Arg Trp Gln Gln Gly Asn Val Phe Ser Cys Ser
            305                 310                 315                 320

Val Met His Glu Ala Leu His Asn His Tyr Thr Gln Lys Ser Leu Ser
                            325                 330                 335

Leu Ser Pro Gly Lys
                            340

<210> SEQ ID NO 30
<211> LENGTH: 6
<212> TYPE: PRT
<213> ORGANISM: Homo sapiens

<400> SEQUENCE: 30

Asn Gln Arg Glu Leu Pro
1               5

<210> SEQ ID NO 31
<211> LENGTH: 6
```

```
<212> TYPE: PRT
<213> ORGANISM: Homo sapiens

<400> SEQUENCE: 31

Met Phe Arg Lys Thr Pro
1               5

<210> SEQ ID NO 32
<211> LENGTH: 6
<212> TYPE: PRT
<213> ORGANISM: Homo sapiens

<400> SEQUENCE: 32

Ser His Cys Leu Pro Ala
1               5

<210> SEQ ID NO 33
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Ser or Thr

<400> SEQUENCE: 33

Asn Gln Xaa Glu Leu Pro
1               5

<210> SEQ ID NO 34
<211> LENGTH: 252
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Arg or Thr
<220> FEATURE:
<221> NAME/KEY: MOD_RES
<222> LOCATION: (123)..(123)
<223> OTHER INFORMATION: Arg or Asn
<220> FEATURE:
<221> NAME/KEY: MOD_RES
<222> LOCATION: (238)..(238)
<223> OTHER INFORMATION: Ala or Asn
<220> FEATURE:
<221> NAME/KEY: MOD_RES
<222> LOCATION: (247)..(247)
<223> OTHER INFORMATION: Gly or Asn

<400> SEQUENCE: 34

Thr Arg His Gln Asp Gly Arg Gln Asn Gln Ser Ser Leu Ser Pro Val
1               5                   10                  15

Leu Leu Pro Arg Asn Gln Xaa Glu Leu Pro Thr Gly Asn His Glu Glu
                20                  25                  30

Ala Glu Glu Lys Pro Asp Leu Phe Val Ala Val Pro His Leu Val Ala
            35                  40                  45

Thr Ser Pro Ala Gly Glu Gly Gln Arg Gln Arg Glu Lys Met Leu Ser
        50                  55                  60

Arg Phe Gly Arg Phe Trp Lys Lys Pro Glu Arg Glu Met His Pro Ser
65                  70                  75                  80

Arg Asp Ser Asp Ser Glu Pro Phe Pro Pro Gly Thr Gln Ser Leu Ile
                85                  90                  95

Gln Pro Ile Asp Gly Met Lys Met Glu Lys Ser Pro Leu Arg Glu Glu
            100                 105                 110
```

```
Ala Lys Lys Phe Trp His His Phe Met Phe Xaa Lys Thr Pro Ala Ser
        115                 120                 125

Gln Gly Val Ile Leu Pro Ile Lys Ser His Glu Val His Trp Glu Thr
    130                 135                 140

Cys Arg Thr Val Pro Phe Ser Gln Thr Ile Thr His Glu Gly Cys Glu
145                 150                 155                 160

Lys Val Val Val Gln Asn Asn Leu Cys Phe Gly Lys Cys Gly Ser Val
                165                 170                 175

His Phe Pro Gly Ala Ala Gln His Ser His Thr Ser Cys Ser His Cys
            180                 185                 190

Leu Pro Ala Lys Phe Thr Thr Met His Leu Pro Leu Asn Cys Thr Glu
        195                 200                 205

Leu Ser Ser Val Ile Lys Val Val Met Leu Val Glu Glu Cys Gln Cys
    210                 215                 220

Lys Val Lys Thr Glu His Glu Asp Gly His Ile Leu His Xaa Gly Ser
225                 230                 235                 240

Gln Asp Ser Phe Ile Pro Xaa Val Ser Ala Thr Gly
                245                 250

<210> SEQ ID NO 35
<211> LENGTH: 6
<212> TYPE: PRT
<213> ORGANISM: Homo sapiens

<400> SEQUENCE: 35

Pro Ala Arg Lys Arg Trp
1               5

<210> SEQ ID NO 36
<211> LENGTH: 6
<212> TYPE: PRT
<213> ORGANISM: Homo sapiens

<400> SEQUENCE: 36

Ser Arg Arg Arg Val Lys
1               5

<210> SEQ ID NO 37
<211> LENGTH: 168
<212> TYPE: PRT
<213> ORGANISM: Homo sapiens
<220> FEATURE:
<221> NAME/KEY: MOD_RES
<222> LOCATION: (55)..(55)
<223> OTHER INFORMATION: Arg or Asn
<220> FEATURE:
<221> NAME/KEY: MOD_RES
<222> LOCATION: (57)..(57)
<223> OTHER INFORMATION: Gln or Thr
<220> FEATURE:
<221> NAME/KEY: MOD_RES
<222> LOCATION: (131)..(131)
<223> OTHER INFORMATION: Arg or Asn
<220> FEATURE:
<221> NAME/KEY: MOD_RES
<222> LOCATION: (133)..(133)
<223> OTHER INFORMATION: Arg or Thr
<220> FEATURE:
<221> NAME/KEY: MOD_RES
<222> LOCATION: (150)..(150)
<223> OTHER INFORMATION: Arg or Asn
<220> FEATURE:
<221> NAME/KEY: MOD_RES
<222> LOCATION: (151)..(151)
<223> OTHER INFORMATION: Arg or Ala
<220> FEATURE:
```

```
<221> NAME/KEY: MOD_RES
<222> LOCATION: (152)..(152)
<223> OTHER INFORMATION: Val or Ser

<400> SEQUENCE: 37

Gly Arg Pro Glu Pro Gln Ser Pro Arg Pro Gln Ser Trp Ala Ala Ala
1               5                   10                  15

Asn Gln Thr Trp Ala Leu Gly Pro Gly Ala Leu Pro Pro Leu Val Pro
            20                  25                  30

Ala Ser Ala Leu Gly Ser Trp Lys Ala Phe Leu Gly Leu Gln Lys Ala
            35                  40                  45

Arg Gln Leu Gly Met Gly Xaa Leu Xaa Arg Gly Gln Asp Glu Val Ala
        50                  55                  60

Ala Val Thr Leu Pro Leu Asn Pro Gln Glu Val Ile Gln Gly Met Cys
65                  70                  75                  80

Lys Ala Val Pro Phe Val Gln Val Phe Ser Arg Pro Gly Cys Ser Ala
                85                  90                  95

Ile Arg Leu Arg Asn His Leu Cys Phe Gly His Cys Ser Ser Leu Tyr
                100                 105                 110

Ile Pro Gly Ser Asp Pro Thr Pro Leu Val Leu Cys Asn Ser Cys Met
            115                 120                 125

Pro Ala Xaa Lys Xaa Trp Ala Pro Val Val Leu Trp Cys Leu Thr Gly
        130                 135                 140

Ser Ser Ala Ser Arg Xaa Xaa Xaa Lys Ile Ser Thr Met Leu Ile Glu
145                 150                 155                 160

Gly Cys His Cys Ser Pro Lys Ala
                165
```

CERBERUS/COCO DERIVATIVES AND USES THEREOF

RELATED APPLICATIONS

This application is a continuation-in-part of U.S. application Ser. No. 12/940,740, filed Nov. 5, 2010, which is a divisional of U.S. application Ser. No. 12/001,494, filed Dec. 10, 2007, now U.S. Pat. No. 7,833,971, which claims the benefit of U.S. Provisional Application 60/873,933, filed Dec. 8, 2006, and a continuation-in-part of U.S. application Ser. No. 13/533,733, filed Jun. 26, 2012, which is a continuation of U.S. application Ser. No. 11/597,182, filed Mar. 22, 2010, now abandoned, which is a national-stage filing under 35 U.S.C. 371 of International Application PCT/US05/18928, filed May 27, 2005, which claims the benefit of U.S. Provisional Application Ser. No. 60/575,062, filed May 27, 2004. The specifications of each of the foregoing applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 22, 2013, is named PHPH-P05-005_SEQ.txt and is 46,738 bytes in size.

BACKGROUND

Transforming growth factor-β superfamily proteins represent a large family of cytokines that includes the TGF-βs, activins, inhibins, bone morphogenetic proteins (BMPs) and Mullerian-inhibiting substance (MIS) (for review, see Massague et al., Trends Cell Biol. 7:187-192, 1997). These proteins contain a conserved C-terminal cystine-knot motif, and serve as ligands for diverse families of plasma membrane receptors. Members of the TGF-β family exert a wide range of biological effects on a large variety of cell types. For example, they regulate cell growth, differentiation, matrix production and apoptosis. Many of them have important functions during embryonal development in pattern formation and tissue specification; in the adult, they are involved in processes such as tissue repair and modulation of the immune system.

Activities of the TGF-β superfamily proteins are regulated through various means. One of the negative regulations for the BMP subfamily of proteins is through a relatively large family of so-called Bone Morphogenetic Protein (BMP) antagonists/repressors. These BMP repressors represent a subgroup of proteins that bind BMPs, and interfere with BMP binding to their membrane receptors, thereby antagonizing their actions during development and morphogenesis.

The BMP repressors can be further divided into three groups of proteins based on structural analysis, especially the number of structurally conserved Cys residues in their C-terminal characteristic "Cys-knot" structures: the 8-, 9-, or 10-member ring Cys-knot BMP repressors. The 8-member ring (CAN subfamily) repressors can be divided further into four subgroups based on a conserved arrangement of additional cysteine residues—gremlin and PRDC, Cerberus and coco, and DAN, together with USAG-1 and sclerostin. Orthologs of these human BMP antagonists in the genomes of several model organisms have also been identified, and their phylogenetic relationship has been analyzed (Avsian-Kretchmer and is Hsueh, Mol Endocrinol. 18(1): 1-12, 2004. Epub 2003 Oct. 2, incorporated herein by reference).

Myostatin, or growth/differentiation factor 8 (GDF-8), also belongs to the transforming growth factor-β (TGF-β) superfamily (McPherron et al., Nature 387:83-90 (1997)). The human myostatin gene has been cloned (Nestor et al. Proc. Natl. Acad. Sci. 95:14938-43 (1998)), and it has been reported that myostatin immunoreactivity is detectable in human skeletal muscle in both type 1 and type 2 fibers. With respect to function, myostatin may play a role in negatively regulating the growth and development of skeletal muscle (Nestor et al., supra).

A study with myostatin knock-out mice provided the first evidence that myostatin is a key negative regulator of muscle development (McPherron et al., Nature 387:83-90 (1997)). In the myostatin null mice, the animals were significantly larger than wild-type mice and had a large and widespread increase in skeletal muscle mass. Furthermore, two breeds of cattle, characterized by increased muscle mass, have mutations in the myostatin coding sequence (McPherron et al., Proc. Natl. Acad. Sci. 94:12457-61 (1997)). A naturally occurring myostatin reduced-function mutation in a human child is associated with gross muscle hypertrophy and a family history of exceptional strength. (Williams M S, N Engl J Med. 2004 Sep. 2; 351(10):1030-1; author reply 1030-1.)

Additionally, it should be noted that the serum and intramuscular concentrations of immunoreactive myostatin are increased in HIV-infected men with muscle wasting compared with healthy men, and correlate inversely with the fat-free mass index. These data support the hypothesis that myostatin is a negative regulator of skeletal muscle growth in adult men and contributes to muscle wasting in HIV-infected men (Nestor et al., supra).

In view of the above findings, a need exists for a manner of regulating myostatin activity, particularly in individuals who experience muscle wasting as a result of a condition or disease state such as, for example, aging, Autoimmune Deficiency Syndrome (AIDS), Multiple Sclerosis, and cancer. The present invention provides methods and compositions which may be utilized to help individuals with such muscle wasting conditions and provides further insight into the regulation of myostatin gene expression.

SUMMARY OF THE INVENTION

One aspect of the invention provides a pharmaceutical preparation of Cerberus, Coco or other polypeptide from the Cerberus/Dan/Gremlin superfamily (collectively herein "CDG proteins") for inhibiting the function/signaling of Nodal, myostatin and BMP. Exemplary preparations of the subject CDG polypeptides may include variant Cerberus or Coco sequences that substantially retain the binding affinity of the parent protein to Nodal, myostatin and/or another BMP (such as BMP-4). For instance, the present invention provides pharmaceutical preparations for inhibiting myostatin, comprising a myostatin antagonist protein that includes (at least) a myostatin binding domain of a Cerberus/Dan/Gremlin polypeptide or variant thereof. The myostatin antagonist protein binds to and neutralizes one or more of nodal and/or myostatin. Preferably, the pharmaceutical preparation is substantially free of pyrogenic materials so as to be suitable for administration as a human or veterinarian therapeutic.

These pharmaceutical preparations can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies. These pharmaceutical preparations can also be used to reduce the severity of a pathologic condition, which is characterized, at least in part, by an abnormal amount, development or metabolic activity of heterotopic ossification in tissues such as of muscles, tendons, and ligaments; Osteoarthritis (OA), including the development of osteophytes and synovial thickening; ovarian cancer; Fibrodysplasia ossificans progressiva (FOP); Atherosclerosis, especially inflammatory response in early steps of atherogenesis in lesion-prone areas; and craniosynostoses.

Another aspect of the invention provides a pharmaceutical preparation of CDG protein derivative for specifically inhibiting Nodal and/or myostatin function without substantially compromising BMP (such as BMP-4) signaling (e.g., does not substantially bind BMP-4 or other BMPs). Exemplary preparations of this aspect of the invention include polypeptides including the N-terminal truncated versions of Cerberus or Coco, or other fragments that include the cysteine-core. These so-called "N-terminally truncated CDG derivatives" can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

In certain embodiments, the mysotatin inhibitor is a polypeptide that includes a myostatin binding domain of a CDG protein. For instance, the Cerberus protein variant can be derived from a human, mouse, or other species of Cerberus, including a human or mouse Cerberus variant sequence sharing at least about 50%, 60%, 70%, 80%, 90%, 95%, or 99% or more sequence similarity or identity with the human or mouse Cerberus protein, and substantially retain the binding affinity of wild-type Cerberus for myostatin. Likewise, the Coco protein variant can be derived from a human, mouse, or other species of Coco, including a human or mouse Coco variant sequence sharing at least about 50%, 60%, 70%, 80%, 90%, 95%, or 99% or more sequence similarity or identity with the human or mouse Coco protein, and substantially retain the binding affinity of wild-type Coco for myostatin.

In certain related embodiments, the mysotatin inhibitor is a polypeptide that includes a myostatin binding domain of a CDG protein, which polypeptide does not substantially bind BMP-4 (and other BMPs). For instance, the myostatin binding domain can be derived from a human, mouse, or other species of N-terminally truncated Cerberus, including a human or mouse Cerberus derivative, with amino acid residues starting from any one of residues 106-119 of SEQ ID NO. 2 or 8 of US 2002/0164682 A1 (see below), and ending at any residue after residue 241 of SEQ ID No. 2 or 8 of US 2002/0164682 A1, preferably ending at any residue between residues 241 and 267 of SEQ ID NO. 2 or 8 of US 2002/0164682 A1 (all residue numbers inclusive).

For example, residues 106-119 of human Cerberus (SEQ ID NO:5) is:

```
PPGTQSLIQPIDGM          (SEQ ID NO: 1)
```

Residues 241-267 of human Cerberus is:

```
CKVKTEHEDGHILHAGSQDSFIPGVSA    (SEQ ID NO: 2)
```

Also included are Cerberus derived variant sequence, e.g., N-terminally truncated myostatin binding domain of Cerberus that retains myostatin binding activity but loses other BMP binding activity. Variant sequences may be desirable as a way to alter selectivity of the inhibitor (e.g., relative to GDF-8, GDF-11 or nodal binding), alter other binding characteristics with respect to myostatin (such as $K_d$, and/or $K_{on}$ or $K_{off}$ rates), or improve biodistribution or half life in vivo or on the shelf.

In certain preferred embodiments, the Cerberus polypeptide (full-length or N-terminally truncated) comprising the myostatin binding domain binds myostatin with a $K_d$ of 1 µM or less, and more preferably a $K_d$ of 100 nM, 10 nM or even 1 nM or less.

In certain related embodiments, the mysotatin inhibitor is a polypeptide that includes a myostatin binding domain of a Coco protein, such as the human Coco protein shown in FIG. 3 or in GenBank Accession number 22749329. An exemplary human Coco protein sequence is

```
                                                              (SEQ ID NO: 3)
  1 MLLGQLSTLL  CLLSGALPTG  SGRPEPQSPR  PQSWAAANQT  WALGPGALPP  LVPASALGSW

61 KAFLGLQKAR  QLGMGRLQRG  QDEVAAVTLP  LNPQEVIQGM  CKAVPFVQVF  SRPGCSAIRL

121 RNHLCFGHCS  SLYIPGSDPT  PLVLCNSCMP  ARKRWAPVVL  WCLTGSSASR  RRVKISTMLI

181 EGCHCSPKA
```

In certain preferred embodiments, the Coco polypeptide (full-length or N-terminally truncated) comprising the myostatin binding domain binds myostatin with a $K_d$ of 1 µM or less, and more preferably a $K_d$ of 100 nM, 10 nM or even 1 nM or less.

In certain embodiments, the myostatin binding domain is part of a fusion protein including, in addition to the myostatin binding domain, one or more polypeptide portions that enhance one or more of in vivo stability, in vivo half life, uptake/administration, tissue localization or distribution, formation of protein complexes, and/or purification. For instance, the fusion protein can include an immunoglobulin Fc domain. The fusion protein may include a purification subsequence, such as an epitope tag, a FLAG tag, a polyhistidine sequence, or as a GST fusion.

In certain embodiments, the myostatin binding domain is part of a protein that includes one or more modified amino acid residues, such as a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

In certain embodiments, the subject variant CDG polypeptide is selective for binding and inhibition of myostatin, e.g., relative to GDF-11 and/or nodal. For instance, the variant CDG polypeptide can be one which has a dissociation constant ($K_d$) for myostatin binding that is at least 2 times less than its $K_d$ for binding GDF-11 and/or nodal, and even more preferably at least 5, 10, 100 or even 1000 times less. Whether by virture of binding kinetics or biodistribution, the subject variant CDG polypeptide can also be selected based on relative in vivo potency, such as an inhibitor that has an $EC_{50}$ for inhibiting myostatin activity, or a particular physiological consequence (such as promoting muscle growth, promoting bone density or inducing adipocytes differentiation) that is at least 2 times less than its $EC_{50}$ for inhibiting GDF-11 and/or nodal activities, and even more preferably at least 5, 10, 100 or even 1000 times less.

In certain embodiments, the subject variant CDG polypeptide is selective for binding and inhibition of myostatin, e.g., relative to other BMP proteins such as BMP-4. For instance, the variant CDG polypeptide can be one which has a dissociation constant ($K_d$) for myostatin binding that is at least 2 times less than its $K_d$ for binding BMP-4, and even more preferably at least 5, 10, 100 or even 1000 times less. Whether by virture of binding kinetics or biodistribution, the subject variant CDG polypeptide can also be selected based on relative in vivo potency, such as an inhibitor that has an $EC_{50}$ for inhibiting myostatin activity, or a particular physiological consequence (such as promoting muscle growth, promoting bone density or inducing adipocytes differentiation) that is at least 2 times less than its $EC_{50}$ for inhibiting BMP-4 activities, and even more preferably at least 5, 10, 100 or even 1000 times less.

In certain preferred embodiments, the variant CDG polypeptide binding domain binds myostatin with a $K_d$ of 1 µM or less, and more preferably a $K_d$ of 100 nM, 10 nM or even 1 nM or less.

In general, the subject myostatin inhibtor preparations are suitable for use in a human patients. In preferred embodiments, the subject preparations of variant CDG polypeptides will be substantially free of pyrogenic materials so as to be suitable for administration to a human patient.

In other embodiments, the subject variant CDG polypeptides can be administered to non-human animals, particularly other mammals. For example, the compounds of the present invention can be given to chickens, turkeys, livestock animals (such as sheep, pigs, horses, cattle, etc.), companion animals (e.g., cats and dogs) or may have utility in aquaculture to accelerate growth and improve the protein/fat ratio. To further illustrate, the subject variant Cerberus polypeptides can be used to stimulate growth or enhance feed efficiency of animals raised for meat production to improve carcass quality, or to increase milk production in dairy cattle.

Another aspect of the invention relates to packaged pharmaceuticals comprising a pharmaceutical preparation of a variant CDG polypeptide, as described herein, and a label or instructions for use in promoting growth of muscle tissue in a human patient.

Still another aspect of the invention relates to packaged pharmaceuticals comprising a pharmaceutical preparation of a variant CDG polypeptide, as described herein, and a label or instructions for veterinarian use in promoting growth of muscle tissue in a non-human mammal.

Another aspect of the invention relates to a method for inhibiting myostatin signal transduction in vivo by administering a pharmaceutical preparation of one or more of the subject variant CDG polypeptides. The subject method can be used to promote muscle growth, promote adipogenic differentiation, and/or promote bone growth or mineralization in human patients or in non-human animals.

In certain embodiments, the treatment methods of the present invention can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD).

Exemplary motor neuron diseases that can be treated with a regimen including the subject myostatin include: Amyotrophic Lateral Sclerosis (ALS) (Also known as Lou Gehrig's Disease), Infantile Progressive Spinal Muscular Atrophy (SMA, SMA1 or WH) (Also known as SMA Type 1, Werdnig-Hoffman), Intermediate Spinal Muscular Atrophy (SMA or SMA2) (Also known as SMA Type 2), Juvenile Spinal Muscular Atrophy (SMA, SMA3 or KW) (Also known as SMA Type 3, Kugelberg-Welander), Spinal Bulbar Muscular Atrophy (SBMA) (Also known as Kennedy's Disease and X-Linked SBMA), and Adult Spinal Muscular Atrophy (SMA).

Exemplary inflammatory myopathies that can be treated with a regimen including the subject myostatin include: Dermatomyositis (PM/DM), Polymyositis (PM/DM), and Inclusion Body Myositis (IBM).

Exemplary diseases of the neuromuscular junction that can be treated with a regimen including the subject myostatin include: Myasthenia Gravis (MG), Lambert-Eaton Syndrome (LES), and Congenital Myasthenic Syndrome (CMS).

Exemplary myopathies due to endocrine abnormalities that can be treated with a regimen including the subject myostatin include: Hyperthyroid Myopathy (HYPTM) and Hypothyroid Myopathy (HYPOTM).

Exemplary diseases of peripheral nerve that can be treated with a regimen including the subject myostatin include: Charcot-Marie-Tooth Disease (CMT), Dejerine-Sottas Disease (DS), and Friedreich's Ataxia (FA).

Other exemplary myopathies that can be treated with a regimen including the subject myostatin include: Myotonia Congenita (MC), Paramyotonia Congenita (PC), Central Core Disease (CCD), Nemaline Myopathy (NM), Myotubular Myopathy (MTM or MM), and Periodic Paralysis (PP).

Exemplary metabolic diseases of muscle that can be treated with a regimen including the subject myostatin include: Phosphorylase Deficiency (MPD or PYGM), Acid Maltase Deficiency (AMD), Phosphofructokinase Deficiency (PFKM), Debrancher Enzyme Deficiency (DBD), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD).

The subject method can also be used to prevent, ameliorate or reduce the severity of a metabolic disorder, such as in the treatment of obesity or type II diabetes. To further illustrate, the subject variant CDG polypeptide preparations can be used to decrease body fat proportion in a subject.

In still other embodiments, the variant CDG polypeptide preparations can be used as part of such methods as: treating or preventing congestive heart failure; for reducing frailty associated with aging; increasing bone density (such as for treating osteoporosis) or accelerating bone fracture repair; treating growth retardation, treatment of physiological short stature, attenuating protein catabolic response such as after a major operation; reducing protein loss due to chronic illness; accelerating wound healing; accelerating the recovery of burn patients or patients having undergone major surgery; maintenance of skin thickness; metabolic homeostasis and renal homeostasis. Still other uses of the subject variant CDG polypeptides include: treating growth hormone deficient adults and preventing catabolic side effects of glucocorticoids.

The subject pharmaceutical composition can also be used as myostatin antagonist to treat a number of neuronal system disease conditions, including CNS injuries/disease such as spinal cord injury and stroke, and PNS injuries/diseases.

The present invention also contemplates the use of the subject myostatin formulations conjointly with one or more other compounds useful in an effort to treat the diseases or therapeutic indications enumerated above. In these combinations, the therapeutic agents and the variant CDG polypeptides of this invention may be independently and sequentially administered or co-administered. Combined therapy to inhibit bone resorption, prevent osteoporosis, reduce skeletal fracture, enhance the healing of bone fractures, stimulate bone formation and increase bone mineral density can be effectuated by combinations of bisphosphonates and the variant CDG polypeptides of this invention. Bisphosphonates with these utilities include but are not limited to alendronate, tiludronate, dimethyl-APD, risedronate, etidronate, YM-175, clodronate, pamidronate, and BM-210995 (ibandronate).

The subject mysostatin inhibitors may be combined with a mammalian estrogen agonist/antagonist. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. A variety of these compounds are described and referenced below, however, other estrogen agonists/antagonists will be known to those skilled in the art. Exemplary estrogen agonist/antagonists include droloxifene and associated compounds (see U.S. Pat. No. 5,047,431), tamoxifen and associated compounds (see U.S. Pat. No. 4,536,516), 4-hydroxy tamoxifen (see U.S. Pat. No. 4,623,660), raloxifene and associated compounds (see 4 U.S. Pat. No. 4,418,068), and idoxifene and associated compounds (see U.S. Pat. No. 4,839,155).

The subject mysostatin inhibitors may also be combined with one or more of the following agents: glutamate antagonists (including partial antagonists) such as riluzole and topiramate; polypeptide growth factors, such as growth hormone (GH) and insulin-like growth factor 1 (IGF-1), or drugs that increases the body's own production of neurotrophic factors, such as xaliproden; anti-inflammatory agents, such as celecoxib (Celebrex) and other COX-2 inhibitors; antibiotics, such as minocycline (Minocin, Dynacin) or other agents that inhibit caspase enzymes; Protein kinase C inhibitors such as tamoxifen (Nolvadex); and various over-the-counter substances, including vitamin E, coenzyme Q10 and creatine.

BRIEF DESCRIPTION OF THE DRAWINGS

FIG. 3 Coco, a BMP inhibitor. (A) Nucleotide sequence of *Xenopus* Coco (SEQ ID NO: 11) and the corresponding translated amino acid sequence (SEQ ID NO: 12). (B) Alignment at the amino acid level of *Xenopus* (SEQ ID NO: 13), Fugu (SEQ ID NO: 16), human (SEQ ID NO: 15) and mouse (SEQ ID NO: 14) Coco and other family members, *Xenopus* Cerberus (SEQ ID NO: 17), human Cerberus (SEQ ID NO: 18), chicken Cerberus (SEQ ID NO: 19) and chicken Caronte (SEQ ID NO: 20). See Bell et al. (2003) Development 130(7): 1381-1389 which is incorporated by reference herein.

DETAILED DESCRIPTION

I. Overview

Figure 1:
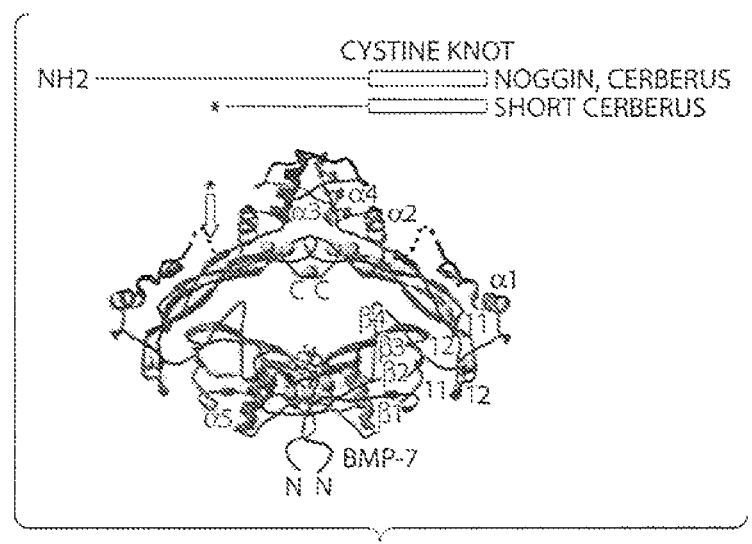
FIG. 1 is a schematic drawing of a full-length and an N-terminally truncated version of Cerberus, showing the intact C-terminal Cys-knot domain. The lower panel shows the predicted position of the N-terminal deletion of Cerberus, based on the crystal structure of Noggin bound to BMP-7.
Figure 2:
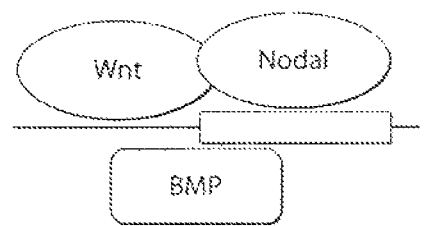
FIG. 2 shows a schematic drawing of where Wnt, Nodal and BMP bind to Cerberus. BMP-2 and the highly related BMP-4 competitively bind Cerberus, likely in the same region. Other more distantly related or unrelated proteins, such as TGF-beta1, EGF, and PDGF, do not compete with BMP-4. The N-terminally truncated version of Cerberus still binds Xnr-1 (*Xenopus* homolog of mouse Nodal).

Cerberus is expressed in the anterior endomesoderm (Bouwmeester et al., Nature 382: 595-601, 1996; Piccolo et al., Nature 397: 707-10, 1999; Rodriguez et al., Nature 401: 243-51, 1999) during development. Caronte, a chick ortholog, is involved in left-right asymmetry in the chick embryo (Rodriguez, supra). Cerberus functions as a multivalent growth factor antagonist in the extracellular space and inhibits signaling by BMP-4, nodal, and Wnt (Belo et al., Genesis 26: 265-70, 2000). Mouse Cerberus binds to BMP proteins and nodal via independent sites (Piccolo, supra), whereas the *Xenopus* Cerberus also binds Wnt proteins and inhibits their actions (Belo, supra). Cerberus has the unique property of inducing ectopic heads in the absence of trunk structures (Piccolo, supra). The expression of Cerberus during gastrulation is activated by nodal-related signals in endoderm and by Spemann-organizer factors (Yamamoto et al., Dev Biol 257: 190-204, 2003).

Orthologs for Cerberus can be found in *Xenopus tropicalis* and *Fugu rubripes*, but are missing in invertebrates. In *Fugu rubripes*, there is only one ortholog for Cerberus. All orthologous genes for Cerberus have two exons; the first eight amino acids of the cystine-knot domain are encoded by the 3' end of the first exon and the remainder of the motif by the second exon. In some orthologs, a predicted proteolytic cleavage site can be found upstream of the beginning of the cystine-knot domain.

Coco is another member of the Cerberus/Dan family of proteins that inhibits Nodal signaling.

In part, the present invention provides Coco or Cerberus derivatives for inhibiting Nodal, GDF-11 and/or myostatin function. In certain embodiments, the Coco and Cerberus derivatives inhibit Nodal, GDF-11 and/or myostatin function without substantially compromising BMP (such as BMP-4) signaling (e.g., does not substantially bind BMP-4 or other BMPs). The subject Cerberus derivatives may also be used to inhibit BMP (such as BMP-4) signaling.

Exemplary preparations of the subject invention include Cerberus polypeptide derivatives, including the N-terminal truncated versions of Cerberus. These so-called "Cerberus derivatives" can be used to reduce the severity of a pathologic condition, which is characterized, at least in part, by an abnormal amount, development or metabolic activity of muscle or adipose tissue in a subject. For instance, the pharmaceutical preparations of the present invention can be administered in an amount effective to prevent, ameliorate or reduce the severity of a wasting disorder, such as cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies.

II. Definitions

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope an meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants/sequence variants Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

A nucleic acid molecule is "hybridizable" to another nucleic acid molecule, such as a cDNA, genomic DNA, or RNA, when a single stranded form of the nucleic acid molecule can anneal to the other micleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS).

Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringent condition" is well understood in the art to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning*, 2$^{nd}$ ed., Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$, for hybrids of nucleic acids having those sequences. The relative stability (corresponding to higher $T_m$) of micleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

"Polypeptide," "peptide" or "protein" are used interchangeably to describe a chain of amino acids that are linked together by chemical bonds called "peptide bonds." A protein or polypeptide, including an enzyme, may be a "native" or "wild-type," meaning that it occurs in nature; or it may be a "mutant," "variant," or "modified," meaning that it has been made, altered, derived, or is in some way different or changed from a native protein or from another mutant.

As used herein, the terms "Cerberus/Dan/Gremlin superfamily protein" and "CDG protein" are both used to signify the protein family which comprises Cerberus, Coco and other related proteins.

"Cerberus or Cerberus-like protein" refers to mammalian Cerberus and Cerberus-like proteins, such as the murine (NCBI RefSeq ID NP_034017) or human (NCBI RefSeq ID NP_005445) Cerberus proteins (also see SEQ ID NOs. 2 and 8, respectively, of US 2002/0164682 A1, the entire contents of which is incorporated herein by reference), and other proteins which share sequence homology to the highly conserved cysteine pattern of the C-terminal portion of the mammalian Cerberus proteins. Exemplary amino acid sequences for Cerberus proteins include Murine Cerberus protein (NCBI RefSeq ID NP_034017):

```
                                                          (SEQ ID NO: 4)
  1 mhlllvqllv llplgkadlc vdgcqsqgsl sfpllergrr dlhvanheea edkpdlfvav 61 phlmgtslag egqrqrgkml srlgrfwkkp etefypprdv esdhvssgmq avtqpadgrk 121 versplqeea krfwhrfmfr kgpafqgvil pikshevhwe tcrtvpfnqt iahedcqkvv 181 vqnnlcfgkc ssirfpgega dahsfcshcs ptkfttvhlm lnctsptpvv kmvmqveecq 241 cmvktergee rlllagsqgs fipglpaskt np
```

Human Cerberus protein (NCBI RefSeq ID NP_005445):

```
                                                          (SEQ ID NO: 5)
  1 mhlllfqllv llplgktttrh qdgrqnqssl spvllprnqr elptgnheea eekpdlfvav 61 phlvatspag egqrgrekml srfgrfwkkp eremhpsrds dsepfppgtq sliqpidgmk 121 meksplreea kkfwhhfmfr ktpasqgvil pikshevhwe tcrtvpfsqt ithegcekvv 181 vqnnlcfgkc gsvhfpgaaq hshtscshcl pakfttmhlp lnctelssvi kvvmlveecq 241 ckvktehedg hilhagsqds fipgvsa
```

The mouse and human Cerberus are as disclosed in US 2002/0164682 A1, as SEQ ID NOs. 1 and 7 (incorporated herein by reference).

NCBI RefSeq ID NM_005454.1 (human Cerberus mRNA).

(SEQ ID NO: 6)

```
  1 atgcatctcc tcttatttca gctgctggta ctcctgcctc taggaaagac cacacggcac
 61 caggatggcc gccagaatca gagttctctt tcccccgtac tcctgccaag gaatcaaaga
121 gagcttccca caggcaacca tgaggaagct gaggagaagc cagatctgtt tgtcgcagtg
181 ccacaccttg tagccaccag ccctgcaggg gaaggccaga ggcagagaga aagatgctg
241 tccagatttg gcaggttctg gaagaagcct gagagagaaa tgcatccatc cagggactca
301 gatagtgagc ccttcccacc tgggacccag tccctcatcc agccgataga tggaatgaaa
361 atggagaaat ctcctcttcg ggaagaagcc aagaaattct ggcaccactt catgttcaga
421 aaaactccgg cttctcaggg ggtcatcttg cccatcaaaa gccatgaagt acattgggag
481 acctgcagga cagtgccctt cagccagact ataacccacg aaggctgtga aaagtagtt
541 gttcagaaca acctttgctt tgggaaatgc gggtctgttc attttcctgg agccgcgcag
601 cactcccata cctcctgctc tcactgtttg cctgccaagt tcaccacgat gcacttgcca
661 ctgaactgca ctgaactttc ctccgtgatc aaggtggtga tgctggtgga ggagtgccag
721 tgcaaggtga agacggagca tgaagatgga cacatcctac atgctggctc ccaggattcc
781 tttatcccag gagtttcagc ttga
```

NM_009887.1 (mouse Cerberus mRNA).

(SEQ ID NO: 7)

```
   1 gggggggggg ggggtcagag ggagcttcct tttaggcccg tccatctgtg aatctaacct
  61 cagtttctgg gaatcaggaa gcatgcatct cctcttagtt cagctgcttg ttctcttgcc
 121 tctggggaag gcagacctat gtgtggatgg ctgccagagt cagggctctt tatcctttcc
 181 tctcctagaa aggggtcgca gagatctcca cgtggccaac cacgaggagg cagaagacaa
 241 gccggatctg tttgtggccg tgccacacct catgggcacc agcctggctg ggaaggcca
 301 gaggcagaga gggaagatgc tgtccaggct tggaagattc tggaagaaac ctgagaccga
 361 attttacccc ccaagggatg tggaaagcga tcatgtctca tcggggatgc aggccgtgac
 421 tcagccagca gatgggagga aagtggagag atcacctcta caggaggaag ccaagaggtt
 481 ctggcatcgg ttcatgttca gaaagggccc ggcgttccag ggagtcatcc tgcccatcaa
 541 aagccacgaa gtacactggg agacctgcag gactgtgccc ttcaaccaga ccattgccca
 601 tgaagactgt caaaaagtcg ttgtccagaa caaccttgc tttggcaaat gcagttccat
 661 tcgtttccc ggagaagggg cagatgccca gcttctgc tcccactgct cgccccaccaa
 721 attcaccacc gtgcacttga tgctgaactg caccagccca accccgtgg tcaagatggt
 781 gatgcaagta gaagagtgtc agtgcatggt gaagacggaa cgtggagagg agcgcctcct
 841 actggctggt tcccagggtt ccttcatccc tggacttcca gcttcaaaaa caaacccatg
 901 aattacctca acagaaagca aaacctcaac agaataagtg agggttattc aatctggaaa
 961 tgttatgtga gttatataaa gatcagtgga aaatatcttt ctctctccct ctctcccct
1021 ctctcttctc tctattttct ctctctctct ctctctctct ctctctctct ctctctctca
1081 cacacacaca cacacacaca cacacacaca catgtttgtg tttagacagg gtcttatgta
1141 ttctcagctg gcctcaaact cacaatgtgg ctggggatga ttttaaactc ctgatccaat
1201 tcctgagtgc tgggattaca gacatgctcc ataanacata gctcccagaa ggattttaa
1261 aagagatttt gcatgtttca aagttgcctt tgagactcag aaatattttg atntattgaa
1321 tggccttgcc acagatgtgg gaggcagctt gcttggtggc ccaagtattt tttttttgtt
1381 cgttcagaat tctccacatg aagtttttac tgttggttat ctggcgttga agaaggaata
```

-continued

```
1441 gtgaaggtac ttttaacagt ttacacgtgg aaggggctca ggcactagga accaacettt 1501 tcccggaata tgaggaaaat acatgaacag tattagagtc acttgaggaa gttactagga 1561 aacgccataa gtctccaagt acattgtgag tcattttgaa ggacaatcgt gtatatagac 1621 gaaatcttct actcgtatgc ttttgaatct tctagcaagt taggtttcta tgtttgggct 1681 tcttcctatt gtctaagagt atgtgtgaca aattcaacct gacaaatacc tcaatggcaa 1741 attctgaccc tg
```

It is also expected that Cerberus related proteins also exist in other species, including family members in *Xenopus*, and *Drosophila*, *C. elegans*, zebrafish, as well as in all mammals, for example, rats, mice and humans. "Cerberus or Cerberus-like proteins" also includes variants of the Cerberus proteins, such as allelic variants or variants induced by mutagenesis or deletions, and fragments of Cerberus proteins which variants and fragments retain myostatin binding activity. "Cerberus-like" proteins is also used to signify the family of proteins sharing structural and/or functional similarity, including those proteins which are described further herein. Such proteins may have amino acid sequences sharing significant sequence identity (e.g., at least about 50%, 60%, 70%, 80%, 90%, 95%, 99% or more) with the human or mouse Cerberus proteins, over the full-length, or at least within the myostatin binding domain of the human or mouse Cerberus. Cerberus-like proteins also include proteins that have amino acid sequences that are encoded by nucleic acid sequences that hybridize under stringent conditions with the coding sequences for human or mouse Cerberus, particularly that portion of the coding sequence for the myostatin binding domain. A Cerberus derivative or variant sequence may or may not lack the N-terminal BMP binding domain.

"Coco or Coco-like protein" refers to mammalian Coco proteins and related homologs, such as the human Coco protein of GenBank Accession 22749329, and other proteins which share sequence homology to the highly conserved cysteine pattern of the C-terminal portion of the mammalian Coco proteins. An exemplary amino acid sequences for human Coco protein is

```
                                                           (SEQ ID NO: 3)
  1 MLLGQLSTLL CLLSGALPTG SGRPEPQSPR PQSWAAANQT WALGPGALPP LVPASALGSW

61 KAFLGLQKAR QLGMGRLQRG QDEVAAVTLP LNPQEVIQGM CKAVPFVQVF SRPGCSAIRL

121 RNHLCFGHCS SLYIPGSDPT PLVLCNSCMP ARKRWAPVVL WCLTGSSASR RRVKISTMLI

181 EGCHCSPKA
```

The human Coco coding sequence is disclosed in GenBank Accession 22749328 (incorporated herein by reference).

```
                                                           (SEQ ID NO: 8)
  1 agtccggaca gacagacagg cagacagacg cacggacaag cagatgctcc ttggccagct 61 atccactctt ctgtgcctgc ttagcggggc cctgcctaca ggctcaggga ggcctgaacc 121 ccagtctcct cgacctcagt cctgggctgc agccaatcag acctgggctc tgggcccagg 181 ggccctgccc ccactggtgc cagcttctgc ccttgggagc tggaaggcct tcttgggcct 241 gcagaaagcc aggcagctgg ggatgggcag gctgcagcgt gggcaagacg aggtggctgc 301 tgtgactctg ccgctgaacc ctcaggaagt gatccagggg atgtgtaagg ctgtgccctt 361 cgttcaggtg ttctcccggc ccggctgctc agccatacgc ctccgaaatc atctgtgctt 421 tggtcattgc tcctctctct acatccctgg ctcggacccc accccactag tcctgtgcaa 481 cagctgtatg cctgctcgca agcgttgggc acccgtggtc ctgtggtgtc tcactggcag 541 ctcagcctcc cgtcgacggg tgaagatatc caccatgctg atcgaggggt gtcactgcag 601 cccaaaagca tgaactgagc atcgtggatg ggtgcacgga gacacgcacc ttggagaaat 661 gaggggagat ggaccaagaa agacgtggac ctggatgatg tactctgggt caagagacca 721 gggatgcagg gttaggcaga caggtcccca gagtcctcac cctgctcccc agacagtaga 781 cacagtgccc gtcctggagt tgcaccactg atagtcacag cacacaatga ttgacaactc 841 acttttttt ttttttttga gatggagtct cgctctgtcg cccaggctgg agtgcagtgg 901 cgcaatctca gctcactgca agctccacct cccgggttta tgccattctc ctgtctcagc
```

-continued

```
 961 ctcccgagta gctgggacta caggcacccg ccaacacgcc cggctaattt ttcgtatttt 1021 tagtaaagac agggtttcac cgtgttagcc aggatggtct ctatctcctg acctcgtgat 1081 ctgcctgcct tggccttatt attttttttt tttaaggaca gagtctctct ctgtcaccca 1141 ggctggagtg caatggcgcg atcttggctc actgtaactt ccacttgcca ggctcaagca 1201 gttctcctgc ctcagcctcc tgagtagctg ggactacagg cacccgccac catgcccagc 1261 taatttttgt attttttagta gagacagagt ttcaccatat tagcctggct ggtctcaaac 1321 tcctggcctc aggtgatctg cccacctcgg cctcccaaag tgctgggatc aaatccactg 1381 ttaatcatta ggctgaactg tctcttatag aatgaggtca aagacactcc cagttgcagg 1441 gagggtagat ggccccaccc agaccgagag acacagtgat gacctcagcc tagggacacc 1501 aaaaaaaaaa aaaaaaaaaa cccaaaccaa aaacgcaaac caaagcaggc aggcagacag 1561 ctgctggggg aaatcctggg gtccttgaga cagaggcagg accctcgtgt tcccagctgc 1621 ctcttgcctt gatagtggtg ctgtgtccct ctcagacccc ccacctgagt ctccacagag 1681 ccccacgcct ggcatggcat tccacagaaa ccataaaggt tggctgagtc c
```

It is also expected that Coco-related proteins also exist in other species, including family members in *Xenopus*, and *Drosophila*, *C. elegans*, zebrafish, as well as in all mammals, for example, rats, mice and non-human primates. "Coco or Coco-like proteins" also includes variants of the naturally occurring Coco proteins, such as allelic variants or variants induced by mutagenesis or deletions, and fragments of Coco proteins which variants and fragments retain myostatin binding activity. "Coco-like" proteins is also used to signify the family of proteins sharing structural and/or functional similarity, including those proteins which are described further herein. Such proteins may have amino acid sequences sharing significant sequence identity (e.g., at least about 50%, 60%, 70%, 80%, 90%, 95%, 99% or more) with the human Coco protein, over the full-length, or at least within the myostatin binding domain of the human Coco. Coco-like proteins also include proteins that have amino acid sequences that are encoded by nucleic acid sequences that hybridize under stringent conditions with the coding sequences for human Coco, particularly that portion of the coding sequence for the myostatin binding domain. A Coco derivative or variant sequence may or may not lack the N-terminal BMP binding domain.

Unless specifically stated otherwise, "Cerberus (derivative) therapeutics" or its grammatical variations include the full-length or the N-terminally truncated versions of Cerberus therapeutics.

As used herein, the term "Cerberus or Cerberus-like activity" refers to one or more of the activities which are exhibited by the mammalian Cerberus-like proteins of the present invention. In particular, "Cerberus or Cerberus-like activity" includes the ability to induce, enhance and/or inhibit the formation, growth, proliferation, differentiation, maintenance of neurons and/or related neural cells and tissues such as brain cells, Schwann cells, glial cells and astrocytes. "Cerberus or Cerberus-like" activity also includes the ability to induce molecular markers of neuroendocrine or ectoderm tissue, such as OTX2, N-CAM, MASH, chromagranin, and AP2, as well as the ability to induce the formation of neurons and/or related neural cells and tissues such as brain cells, Schwann cells, glial cells and astrocytes. "Cerberus or Cerberus-like activity" may also include the ability to regulate the interaction of ligands and their protein receptors. "Cerberus or Cerberus-like activity" may further include the ability to regulate the formation, differentiation, proliferation and/or maintenance of other cells and/or tissue, for example connective tissue, organs and wound healing. In particular, "Cerberus or Cerberus-like activity" may include the ability to enhance and/or inhibit the formation, growth, proliferation, differentiation and/or maintenance of cardiac, spleen, liver, pancreas, stomach, kidney, lung and brain cells and tissue, as well as osteoblasts and bone, chondrocytes and cartilage, tendon, epidermis and muscle. "Cerberus and Cerberus-like activity" also includes the activities of Cerberus and Cerberus-like protein in the assays described in the examples and specification herein.

Cerberus and Cerberus-like nucleotide sequences in mouse and human are as disclosed in US 2002/0164682 A1, as SEQ ID NOs: 1 and 7 (incorporated herein by reference). Also see NCBI RefSeq ID NM_005454.1 (human) and NM_009887.1 (mouse).

In certain related embodiments, the mysotatin inhibitor is a polypeptide that includes a myostatin binding domain of a Coco protein, such as the human Coco protein shown in FIG. 3 or in GenBank Accession number 22749329. An exemplary human Coco protein sequence is

```
                                                        (SEQ ID NO: 3)
  1 MLLGQLSTLL CLLSGALPTG SGRPEPQSPR PQSWAAANQT WALGPGALPP LVPASALGSW

61 KAFLGLQKAR QLGMGRLQRG QDEVAAVTLP LNPQEVIQGM CKAVPFVQVF SRPGCSAIRL

121 RNHLCFGHCS SLYIPGSDPT PLVLCNSCMP ARKRWAPVVL WCLTGSSASR RRVKISTMLI

181 EGCHCSPKA
```

The terms "antibody" and "antibody agent" are used interchangeably herein, and refer to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG).

The term "antigen binding fragment" includes any portion of an antibody that binds to a target epitope. An antigen binding fragment may be, for example, a polypeptide including a CDR3 region, or other fragment of an immunoglobulin molecule which retains the affinity and specificity of the myostatin epitope.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between the subject myostatin neutralizing antibodies and a other proteins. Nevertheless, specific binding, may be distinguished as mediated through specific recognition of the myostatin protein. Typically specific binding results in a much stronger association between the antibody and myostatin protein than between the antibody and other proteins, e.g., GDF11. Specific binding by an antibody to myostatin under such conditions requires an antibody that is selected for its specificity for a particular protein. The affinity constant (Ka, as opposed to Kd) of the antibody binding site for its cognate monovalent antigen is at least $10^7$, usually at least $10^8$, preferably at least $10^9$, more preferably at least $10^{10}$, and most preferably at least $10^{11}$ M. A variety of immunoassay formats are appropriate for selecting antibodies specifically reactive with myostatin. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity.

Immunoassays in the competitive binding format can be used to determine cross-reactivity of antibodies with myostatin, e.g., to identify whether a test antibody is a myostatin neutralizing antibody. For example, the myostatin protein, or a fragment thereof is immobilized to a solid support. Test antibodies are added to the assay compete with the binding of a TGF receptor, such as ActRII or ALK7, to the immobilized antigen. The ability of the test antibodies to compete with the binding of a TGF receptor to the immobilized myostatin antigen is compared.

Similarly, immunoassays in the competitive binding format can be used to determine cross-reactivity determinations, e.g., to determine the specificity of a myostatin neutralizing antibody. For example, the myostatin protein, or the myostatin epitope thereof is immobilized to a solid support. Epitopes from other proteins, such as GDF-11, Nodal or BMP-4 or other proteins having sequence homology with myostatin are added to the assay to compete with the binding of a potential myostatin neutralizing antibody to the immobilized antigen. The ability of the test peptides to compete with the binding of potential myostatin neutralizing antibody with the immobilized myostatin antigen is compared. The percent cross-reactivity of the potential myostatin neutralizing antibody for the other antigens is calculated, using standard calculations. In certain preferred embodiments, the subject myostatin neutralizing antibodies have less than 10% cross-reactivity with GDF-11. In other preferred embodiments, the subject myostatin neutralizing antibodies have less than 1%, 5%, or 10% cross-reactivity with BMP-4.

III. Exemplary Cerberus and Coco Derivatives

In certain embodiments, the mysotatin inhibitor is a Cerberus polypeptide sharing at least about 50%, 60%, 70%, 80%, 90%, 95%, 99% or more sequence identity over the full-length of the human or mouse Cerberus protein (infra).

In certain other embodiments, the mysotatin inhibitor is a polypeptide that includes a Cerberus sequence obtained from human, mouse, or other species, their variants or derivatives, including N-terminally truncated versions of Cerberus. The full-length mouse and human Cerberus proteins, disclosed as SEQ ID NOs: 2 and 8, respectively, in US 2002/0164682 A1, are also disclosed in NCBI RefSeq format below:

Human Cerberus full length protein:

(SEQ ID NO: 5)

```
  1 MHLLLFQLLV LLPLGKTTRH QDGRQNQSSL SPVLLPRNQR ELPTGNHEEA EEKPDLFVAV
 61 PHLVATSPAG EGQRQREKML SRFGRFWKKP EREMHPSRDS DSEPFPPGTQ SLIQPIDGMK
121 MEKSPLREEA KKFWHHFMFR KTPASQGVIL PIKSHEVHWE TCRTVPFSQT ITHEGCEKVV
181 VQNNLCFGKC GSVHFPGAAQ HSHTSCSHCL PAKFTTMHLP LNCTELSSVI KVVMLVEECQ
241 CKVKTEHEDG HILHAGSQDS FIPGVSA
```

Residues 106-119 (from any one of which residues the subject Cerberus derivatives may begin), and residues 241-267 (to any one of which residues the subject Cerberus derivatives may end) are underlined.

Mouse Cerberus full length protein:

(SEQ ID NO: 4)

```
  1 MHLLLVQLLV LLPLGKADLC VDGCQSQGSL SFPLLERGRR DLHVANHEEA EDKPDLFVAV
 61 PHLMGTSLAG EGQRQRGKML SRLGRFWKKP ETEFYPPRDV ESDHVSSGMQ AVTQPADGRK
121 VERSPLQEEA KRFWHRFMFR KGPAFQGVIL PIKSHEVHWE TCRTVPFNQT IAHEDCQKVV
181 VQNNLCFGKC SSIRFPGEGA DAHSFCSHCS PTKFTTVHLM LNCTSPTPVV KMVMQVEECQ
241 CMVKTERGEE RLLLAGSQGS FIPGLPASKT NP
```

Residues 106-119 (from any one of which residues the subject Cerberus derivatives may begin), and residues 241-272 (to any one of which residues the subject Cerberus derivatives may end) are underlined. Note that the mouse protein is largely homologous to the human protein throughout the sequences, with the exception of 5 additional residues at the C-terminus. Therefore, whenever a non-human Cerberus derivative is used, the residue numbers refers to those corresponding to the human sequences.

As described above, in certain embodiments, preferred fragments of the human Cerberus derivative proteins are ones which begins anywhere from residues 106-119 (inclusive) at the N-terminus, and ends anywhere after residue 241.

Also included are Cerberus derived variant sequence, including mutants or variants of the wild-type myostatin binding domains that retain myostatin binding activity, optionally substantially loses BMP-4 binding. Variant sequences without BMP binding affinity may be desirable as a way to alter selectivity of the inhibitor (e.g., relative to GDF-11 or nodal binding, where preferential binding to one of the proteins occur. Also includes more preferential—higher affinity than wild-type—binding to myostatin, or more discrimitory—lower affinity than wild-type truncated version—binding to BMP-4), alter other binding characteristics with respect to myostatin (such as $K_d$, and/or $K_{on}$ or $K_{off}$ rates), or improve biodistribution or half life in vivo or on the shelf.

Certain other Cerberus sequences are listed below based on homology search in databases of identified proteins, and the subject variant Cerberus polypeptides can be derived from those proteins as well. Since these sequences are retrieved from public databases available on the internet, additional homologs of the proteins in other species may be obtained as these databases are being updated. Furthermore, other species of Cerberus proteins, especially those of mammals, can be readily obtained by standard molecular biology protocols, such as PCR, low stringency hybridization, Ab-mediated screening of expression libraries using antibodies cross-reacting with identified Cerberus homologs in target species, etc.

For example, sequence alignments using softwares such as DNAStar's MegaAlign (supra) can identify the most conserved regions in the known members of a protein family. PCR can then be carried out using degenerate oligoes covering such most conserved regions, and templates DNA from the target organism. In preferred embodiments, such conserved regions include the kinase domain, and/or the ligand binding domain.

These same conserved regions may be used to generate probes for screening nucleic acid libraries at moderate to low stringency hybridization conditions (see definition section).

*Xenopus* homolog: gi|1513088.

Fugu rubripes: FuguGenscan_32561/SIN-FRUP00000076662.

In certain embodiments, the mysotatin inhibitor is a Cerberus polypeptide sharing at least about 50%, 60%, 70%, 80%, 90%, 95%, 99% or more sequence identity over the full-length of the human or mouse Cerberus protein (infra).

In certain other embodiments, the mysotatin inhibitor is a polypeptide that includes a Coco sequence obtained from human, mouse, or other species, their variants or derivatives, including N-terminally truncated versions of Coco. The full-length human Coco protein is disclosed above.

The various Cerberus and Coco polypeptides may be prepared as fusion proteins. A fusion protein may include one or more additional polypeptide portion that enhance one or more of in vivo stability, in vivo half life, uptake/administration, tissue localization or distribution, formation of protein complexes, and/or purification. For example, a fusion protein may include an immunoglobulin Fc domain and/or a purification subsequence selected from: an epitope tag, a FLAG tag, a polyhistidine sequence, and a GST fusion. The myostatin antagonist protein may include one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

A fusion protein or coupled protein system (e.g. non-fusion covalent linkage by crosslinking) may also include a second myostatin inhibitor domain, which is a polypeptide affinity reagent that selectively binds to myostatin and competes with the binding of an ALK7 or ALK4 receptor. The affinity reagent may be an antibody agent. An antibody agent may be, for example, a recombinant antibody; a monoclonal antibody; a VH domain; a VL domain; an scFv; an Fab fragment; an Fab' fragment; an F(ab')2; an Fv; or a disulfide linked Fv, a fully human antibody or a humanized chimeric antibody, or an antigen binding fragment thereof. An affinity reagent is a peptide or scaffolded peptide that selectively binds to myostatin and competes with the binding of an ALK7 or ALK4 receptor. An affinity reagent may include a myostatin binding domain of ALK7 or ALK4. For example, an extracellular domain of ALK7 or ALK4 (preferably human ALK7 or ALK4) may be used. The affinity reagent may be a small organic molecule that selectively binds to myostatin and competes with the binding of an ALK7 or ALK4 receptor.

An example of a human ALK7 myostatin binding domain is shown below:

(SEQ ID NO: 9)
LKCVCLLCDSSNFTCQTEGACWASVMLTNGKEQVIKSCVSLPELNAQVF

CHSSNNVTKTECCFTDFCNNITLHLP

An example of a human ALK4 myostatin binding domain is shown below:

(SEQ ID NO: 10)
ALLCACTSCLQANYTCETDGACMVSIFNLDGMEHHVRTCIPKVELVPAGK

PFYCLSSEDLRNTHCCYTDY

As shown herein, Caronte, and therefore human Cerberus and presumably Coco also, does not substantially inhibit Activin A signaling in an A204 Reporter Gene Assay. Thus, such myostatin antagonists will preferably exhibit little or no interaction with Activin A-mediated signaling.

IV. Examplary Therapeutic Uses

The subject variant Coco and Cerberus polypeptides, such as the full-length and the N-terminally truncated Cerberus derivatives or Coco derivatives, can be used in a number of therapeutic settings to treat a number of diseases resulting from or exacerbated by the presence of myostatin.

In certain embodiments, the subject polypeptides and derivatives thereof are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

In DMD, boys begin to show signs of muscle weakness as early as age 3. The disease gradually weakens the skeletal or voluntary muscles, those in the arms, legs and trunk. By the early teens or even earlier, the boy's heart and respiratory muscles may also be affected. BMD is a much milder version of DMD. Its onset is usually in the teens or early adulthood, and the course is slower and far less predictable than that of DMD. (Though DMD and BMD affect boys almost exclusively, in rare cases they can affect girls.

Until the 1980s, little was known about the cause of any kind of muscular dystrophy. In 1986, the dystrophin gene deficiency was identified as the cause of DMD. BMD results from different mutations in the same gene. BMD patients have some dystrophin, but it's either insufficient in quantity or poor in quality. Having some dystrophin protects the muscles of those with BMD from degenerating as badly or as quickly as those of people with DMD.

Recent researches demonstrate that blocking or eliminating Myostatin function in vivo is can effectively treat at least certain symptoms in DMD and BMD patients (Bogdanovich et al., supra; Wagner et al., supra). Thus, the subject Cerberus derivatives, especially the N-terminally truncated versions thereof, constitute an alternative means of blocking the function of Myostatin in vivo in DMD and BMD patients.

Similarly, the subject Coco or Cerberus derivatives, especially the N-terminally truncated versions thereof, provide an effective means to increase muscle mass in other disease conditions that are in need of muscle growth. For example, Gonzalez-Cadavid et al. (supra) reported that that Myostatin expression correlates inversely with fat-free mass in humans and that increased expression of the Myostatin gene is associated with weight loss in men with AIDS wasting syndrome. By inhibiting the function of Myostatin in AIDS patients, at least certain symptoms of AIDS may be alleviated, if not completely eliminated, thus significantly improving quality of life in AIDS patients.

Since loss of Myostatin function is also associated with fat loss without diminution of nutrient intake (Zimmers et al., supra; McPherron and Lee, supra), the subject Coco or Cerberus derivatives, especially the N-terminally truncated versions thereof, may further be used as a therapeutic agent for slowing or preventing the development of obesity and type II diabetes.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process.

Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of Myostatin in adult mice was found to induce profound muscle and fat loss analogous to that seen in human cachexia syndromes (Zimmers et al., supra), the subject Coco or Cerberus derivatives, especially the N-terminally truncated versions thereof as a pharmaceutical composition can be beneficially used as a Myostatin antagonist/blocker to prevent, treat, or alleviate the symptoms of the cachexia syndrome, where muscle growth is desired.

In certain embodiments, the subject variant Coco or Cerberus polypeptides, particularly the N-terminally truncated Cerberus derivatives, can be used to form pharmaceutical compositions that can be beneficially used to prevent, treat, or alleviate symptoms of a host of diseases involving neurodegeneration. While not wishing to be bound by any particular theory, the subject Cerberus derivatives may antagonize the inhibitory feedback mechanism mediated through the wild-type ALK7 receptor, thus allowing new neuronal growth and differentiation. The subject Cerberus derivative as a pharmaceutical composition can be beneficially used to prevent, treat, or alleviate symptoms of diseases with neurodegeneration, including Alzheimer's Disease (AD), Parkinson's Disease (PD), Amyotrophic Lateral Sclerosis (ALS), Huntington's disease, etc.

Alzheimer's disease (AD) is a chronic, incurable, and unstoppable central nervous system (CNS) disorder that occurs gradually, resulting in memory loss, unusual behavior, personality changes, and a decline in thinking abilities. These losses are related to the death of specific types of brain cells and the breakdown of connections between them.

AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses. AD patients most commonly die from pneumonia, 8 to 20 years from disease onset.

Parkinson's disease (PD) is a chronic, incurable, and unstoppable CNS disorder that occurs gradually and results in uncontrolled body movements, rigidity, tremor, and gait difficulties. These motor system problems are related to the death of brain cells in an area of the brain that produces dopamine—a chemical that helps control muscle activity.

In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden. People with PD usually die from pneumonia.

Amyotrophic lateral sclerosis (ALS; Lou Gehrig's disease; motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles.

Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

The causes of these neurological diseases has remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

Huntington's disease (HD) is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person.

Tay-Sachs disease and Sandhoff disease are glycolipid storage diseases caused by the lack of lysosomal β-hexosaminidase (Gravel et al., in *The Metabolic Basis of Inherited Disease*, eds. Scriver et al., McGraw-Hill, New York, pp. 2839-2879, 1995). In both disorders, $G_{M2}$ ganglioside and related glycolipids substrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., *Hum. Mol. Genet.* 6: 1879-1885, 1997).

It is well-known that apoptosis plays a role in AIDS pathogenesis in the immune system. However, HIV-1 also induces neurological disease. Shi et al. (*J. Clin. Invest.* 98: 1979-1990, 1996) examined apoptosis induced by HIV-1 infection of the central nervous system (CNS) in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is a also a salient feature of prion diseases, such as Creutzfeldt-Jakob disease in human, BSE in cattle (mad cow disease), Scrapie Disease in sheep and goats, and feline spongiform encephalopathy (FSE) in cats.

The subject Cerberus derivatives, including the N-terminally truncated Cerberus derivatives are also useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term peripheral neuropathy encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people. According to statistics gathered by the World Health Organization, an estimated 1.15 million people have leprosy worldwide.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic—no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including Campylobacter jejuni and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the peripheral nervous system (PNS) and the central nervous system (CNS), as well as other body tissues.

Other PNS diseases treatable with the subject Cerberus derivatives, especially the N-terminally truncated Cerberus derivatives include: Brachial Plexus Neuropathies (Diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, $6^{th}$ ed, pp 1351-2); Diabetic Neuropathies (Peripheral, autonomic, and cranial nerve disorders that are associated with disbetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. See Adams et al., Principles of Neurology, $6^{th}$ ed, p1325); Mononeuropathies (Disease or trauma involving a single peripheral nerve in isolation, or out of proportion to evidence of diffuse peripheral nerve dysfunction. Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions); Neuralgia (Intense or aching pain that occurs along the course or distribution of a peripheral or cranial nerve); Peripheral Nervous System Neoplasms (Neoplasms which arise from peripheral nerve tissue. This includes neurofibromas; Schwannomas; granular cell tumors; and malignant peripheral nerve sheath tumors. See DeVita Jr et al., Cancer: Principles and Practice of Oncology, $5^{th}$ ed, pp 1750-1); Nerve Compression Syndromes (Mechanical compression of nerves or nerve roots from internal or external causes. These may result in a conduction block to nerve impulses, due to, for example, myelin sheath dysfunction, or axonal loss. The nerve and nerve sheath injuries may be caused by ischemia; inflammation; or a direct mechanical effect); Neuritis (A general term indicating inflammation of a peripheral or cranial nerve. Clinical manifestation may include pain; paresthesias; paresis; or hyperthesia); Polyneuropathies (Diseases of multiple peripheral nerves. The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance).

In certain embodiments, the subject full-length Coco or Cerberus polypepetides or variants thereof are used as part of a treatment for diseases or conditions characterized by excessive or undesirable levels of BMP, such as the ones described below.

The heterotopic ossification of muscles, tendons, and ligaments is a common problem faced by orthopaedic surgeons. Hannallah et al. (J Bone Joint Surg Am. 2004 January; 86-A (1):80-91) investigated the ability of Noggin (a BMP [bone morphogenetic protein] antagonist) to inhibit heterotopic ossification. Three varying doses of Noggin-expressing muscle-derived stem cells inhibited the heterotopic ossification elicited by BMP-4-expressing muscle-derived stem cells. Each of three varying doses of Noggin-expressing muscle-derived stem cells also significantly inhibited the heterotopic ossification elicited by demineralized bone matrix. All eleven animals that underwent Achilles tenotomy developed heterotopic ossification at the site of the injury in the control limbs. In contrast, the limbs treated with the Noggin-expressing muscle-derived stem cells had a reduction in the formation of heterotopic ossification of 83% and eight of the eleven animals had no radiographic evidence of heterotopic ossification (p<0.05). Thus, delivery of Noggin mediated by muscle-derived stem cells can inhibit heterotopic ossification caused by BMP-4, demineralized bone matrix, and trauma in an animal model, indicating that gene therapy to deliver BMP inhibitors (Noggin or Cerberus) may become a powerful method to inhibit heterotopic ossification in targeted areas of the body. See also Glaser et al. (J Bone Joint Surg Am. 2003 December; 85-A(12):2332-42).

Osteoarthritis (OA) is a joint disease characterized by osteophyte development, fibrosis, and articular cartilage damage. Effects of exogenous transforming growth factor beta (TGFbeta) isoforms and bone morphogenetic proteins (BMPs) suggest a role for these growth factors in the pathogenesis of OA. Scharstuhl et al. (Arthritis Rheum. 2003 December; 48(12):3442-51) used adenoviral overexpression of TGF-beta and BMP antagonists to block the signaling of TGF-beta and BMP. The inhibitors studied include a secreted, pan-specific TGF-beta antagonist called murine latency-associated peptide 1 (mLAP-1), intracellular inhibitory Smad6 (a BMP antagonist), and Smad7 (a TGF-beta/BMP inhibitor). Intraarticular injection of papain caused increased protein expression of several TGF-beta and BMP isoforms in synovium and cartilage. Adenovirus transfection into the joint resulted in a strong expression of the transgenes in the synovial lining. Overexpression of mLAP-1, Smad6, and Smad7 led to a significant reduction in osteophyte formation compared with that in controls. Smad6 and Smad7 overexpression also significantly decreased synovial thickening. Furthermore, the secreted TGF-beta inhibitor mLAP-1 increased articular cartilage PG loss. These results indicate a pivotal role of excessive endogenous TGF-beta and BMP in the development of osteophytes and synovial thickening, implicating excessive endogenous TGFbeta and BMP in the pathogenesis of OA. In contrast, the prevention of cartilage damage by endogenous TGF-beta signifies the protective role of TGF-beta in articular cartilage. Thus the subject Coco or Cerberus pharmaceutical compositions can be used as BMP antagonists to treat OA, including the development of osteophytes and synovial thickening.

In an analysis of normal ovarian surface epithelium (OSE) and ovarian cancer (OC) cells, Shepherd and Nachtigal (Endocrinology. 2003 August; 144(8):3306-14) observed BMP4 mRNA expression and found that primary OC cells produce mature BMP4. In addition, each member of the downstream signaling pathway was expressed in primary OSE and OC cells. Smad1 was phosphorylated and underwent nuclear translocation in normal OSE and OC cells upon treatment with BMP4. Interestingly, the BMP target genes ID1 and ID3 were up-regulated 10- to 15-fold in primary OC cells, compared with a 2- to 3-fold increase in normal OSE. The growth of several primary OC cells was relatively unaltered by BMP4 treatment; however, long-term BMP4 treatment of primary OC cells resulted in decreased cell density as well as increased cell spreading and adherence. These data demonstrate the existence and putative function of BMP signaling in normal OSE and OC cells, and thus the subject Cerberus pharmaceutical preparations can be used to regulate BMP4 signaling in OC pathogenesis.

Fibrodysplasia ossificans progressiva (FOP), a rare genetic disabling disease characterized by heterotopic bone formation, is of special interest for general medicine since the bone morphogenetic proteins (especially BMP-4) involved in its pathogenesis are known to play a role in skeletal morphogenesis, and the gene antagonist to BMP-4 (such as noggin) might be useful in preventing lamellar bone formation. See Blaszczyk et al. (Eur J. Dermatol. 2003 May-June; 13(3):234-7). Thus the subject Cerberus therapeutics may also be used to treat FOP.

Atherosclerosis is now viewed as an inflammatory disease occurring preferentially in arterial regions exposed to disturbed flow conditions, including oscillatory shear stress (OS), in branched arteries. Sorescu et al. (J Biol Chem. 278 (33):31128-35, 2003) suggest that BMP4 is a mechanosensitive, inflammatory factor playing a critical role in early steps of atherogenesis in the lesion-prone areas. Thus the subject Cerberus therapeutics may be used to control BMP-4 induced inflammatory response in early steps of atherogenesis in those areas.

During skull development, the cranial connective tissue framework undergoes intramembranous ossification to form skull bones (calvaria). As the calvarial bones advance to envelop the brain, fibrous sutures form between the calvarial plates. Expansion of the brain is coupled with calvarial growth through a series of tissue interactions within the cranial suture complex. Craniosynostosis, or premature cranial suture fusion, results in an abnormal skull shape, blindness and mental retardation. Recent studies have demonstrated that gain-of-function mutations in fibroblast growth factor receptors (fgfr) are associated with syndromic forms of craniosynostosis. Noggin, an antagonist of bone morphogenetic proteins (BMPs), is required for embryonic neural tube, somites and skeleton patterning. Warren et al. (Nature. 2003 Apr. 10; 422(6932):625-9) show that noggin is expressed postnatally in the suture mesenchyme of patent, but not fusing, cranial sutures, and that noggin expression is suppressed by FGF2 and syndromic fgfr signalling. Since noggin misexpression prevents cranial suture fusion in vitro and in vivo, it is suggested that syndromic fgfr-mediated craniosynostoses may be the result of inappropriate downregulation of noggin expression, leading to abnormally high BMP activity. Thus the subject Cerberus therapeutics may be used to down-regulate BMP activity to prevent or treat such conditions.

V. Exemplary Formulations

The subject compositions may be used alone, or as part of a conjoint therapy with other compounds/pharmaceutical compositions.

The soluble Coco or Cerberus derivative therapeutics, including the N-terminally truncated Cerberus derivative therapeutics for use in the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the therapeutics, its use in the pharmaceutical preparation of the invention is contemplated. Suitable vehicles and their formulation inclusive of other proteins are described, for example, in the book *Remington's Pharmaceutical Sciences* (*Remington's Pharmaceutical Sciences*. Mack Publishing Co., Easton, Pa., USA 1985). These vehicles include injectable "deposit formulations."

Pharmaceutical formulations of the present invention can also include veterinary compositions, e.g., pharmaceutical preparations of the Coco or Cerberus derivative therapeutics suitable for veterinary uses, e.g., for the treatment of live stock (cow, sheep, goat, pig, and horse, etc.) or domestic animals, e.g., cats and dogs.

Methods of invention may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a therapeutic at a particular target site.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. The pharmaceutical compositions of the present invention may be administered by any means that enables the Coco or Cerberus derivatives to reach the targeted cells/tissues/organs. In some embodiments, routes of administration include those selected from the group consisting of oral, intravesically, intravenous, intraarterial, intraperitoneal, local administration into the blood supply of the organ in which the targeted cells reside or directly into the cells. Intravenous administration is the preferred mode of administration. It may be accomplished with the aid of an infusion pump.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, intravesically, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular therapeutic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other non-human mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Combined with certain formulations, the subject Coco or Cerberus derivatives can be effective soluble agents. The therapeutic polypeptide can be provided a fusion peptide along with a second peptide which promotes solubility. To illustrate, the Cerberus derivatives of the present invention can be provided as part of a fusion polypeptide with all or a fragment of the hinge or Fc portion of the immunoglobulin, which can promote solubility and/or serum stability.

The present invention also contemplates a peptidomimetic sequence of the subject polypeptide derivatives as described herein.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" ($8^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Sources of Caronte and Human Cerberus Protein

Caronte-Fc (Cerberus homolog from *Gallus gallus*) was ordered from R&D Systems (Minneapolis, Minn.).

Full-length and N-terminally truncated forms of human Cerberus sequence were cloned into a human CMV derived expression vector, either with or without a C-terminal fusion to an Fc portion of IgG1 (both human and murine IgG1 Fc fusions were produced). These constructs were transiently transfected in HEK293 cells using polyethylenimine (PEI). After culturing, cells were harvested and conditioned media was collected for purification.

The following constructs were tested:

```
Human Cerberus, full length, no Fc (SEQ ID NO: 5)
MHLLLFQLLV LLPLGKTTRH QDGRQNQSSL SPVLLPRNQR ELPTGNHEEA EEKPDLFVAV

PHLVATSPAG EGQRQREKML SRFGRFWKKP EREMHPSRDS DSEPFPPGTQ SLIQPIDGMK

MEKSPLREEA KKFWHHFMFR KTPASQGVIL PIKSHEVHWE TCRTVPFSQT ITHEGCEKVV

VQNNLCFGKC GSVHFPGAAQ HSHTSCSHCL PAKFTTMHLP LNCTELSSVI KVVMLVEECQ

CKVKTEHEDG HILHAGSQDS FIPGVSA

Human Cerberus, full length, Fc (TGGG linker (SEQ ID NO: 27) and Fc, underlined;
native signal sequence underlined with dotted line) (SEQ ID NO: 28)

MHLLLFQLLV LLPLGKTTRH QDGRQNQSSL SPVLLPRNQR ELPTGNHEEA EEKPDLFVAV

PHLVATSPAG EGQRQREKML SRFGRFWKKP EREMHPSRDS DSEPFPPGTQ SLIQPIDGMK

MEKSPLREEA KKFWHHFMFR KTPASQGVIL PIKSHEVHWE TCRTVPFSQT ITHEGCEKVV

VQNNLCFGKC GSVHFPGAAQ HSHTSCSHCL PAKFTTMHLP LNCTELSSVI KVVMLVEECQ

CKVKTEHEDG HILHAGSQDS FIPGVSA TGGGTHTCPP CPAPELLGGP SVFLFPPKPK

DTLMISRTPE VTCVVVDVSH EDPEVKFNWY VDGVEVHNAK TKPREEQYNS TYRVVSVLTV

LHQDWLNGKE YKCKVSNKAL PVPIEKTISK AKGQPREPQV YTLPPSREEM TKNQVSLTCL

VKGFYPSDIA VEWESNGQPE NNYKTTPPVL DSDGSFFLYS KLTVDKSRWQ QGNVFSCSVM

HEALHNHYTQ KSLSLSPGK

Human Cerberus, short form, Fc (TGGG linker (SEQ ID NO: 27) and Fc, underlined)
(SEQ ID NO: 29)
EVHWETCRTV PFSQTITHEG CEKVVVQNNL CFGKCGSVHF PGAAQHSHTS CSHCLPAKFT

TMHLPLNCTE LSSVIKVVML VEECQCKVKT EHEDGHILHA GSQDSFIPGV SA TGGGTHTCPP

CPAPELLGGP SVFLFPPKPK DTLMISRTPE VTCVVVDVSH EDPEVKFNWY VDGVEVHNAK

TKPREEQYNS TYRVVSVLTV LHQDWLNGKE YKCKVSNKAL PVPIEKTISK AKGQPREPQV

YTLPPSREEM TKNQVSLTCL VKGFYPSDIA VEWESNGQPE NNYKTTPPVL DSDGSFFLYS

KLTVDKSRWQ QGNVFSCSVM HEALHNHYTQ KSLSLSPGK
```

Three different leader sequences were considered:

```
(i) Honey bee mellitin (HBML):
                                (SEQ ID NO: 24)
MKFLVNVALVFMVVYISYIYA (ii) Tissue Plasminogen Activator (TPA):
                                (SEQ ID NO: 25)
MDAMKRGLCCVLLLCGAVFVSP (iii) Native:
                                (SEQ ID NO: 26)
MLLGQLSTLL CLLSGALPTG S.
```

A heterologous or native leader sequence may be fused to the protein sequence at any position within the first 30 amino acids. Modeling suggests that the native leader would yield a product beginning with "TRH . . ." at position 18. Analysis of products expressed herein indicates that the native leader more typically yields a product beginning "KTT . . . " at position 16. Therefore, heterologous leader sequences may be fused N-terminal to position 16 or position 18.

Example 2

Caronte Binds GDF-11

Figure 4:
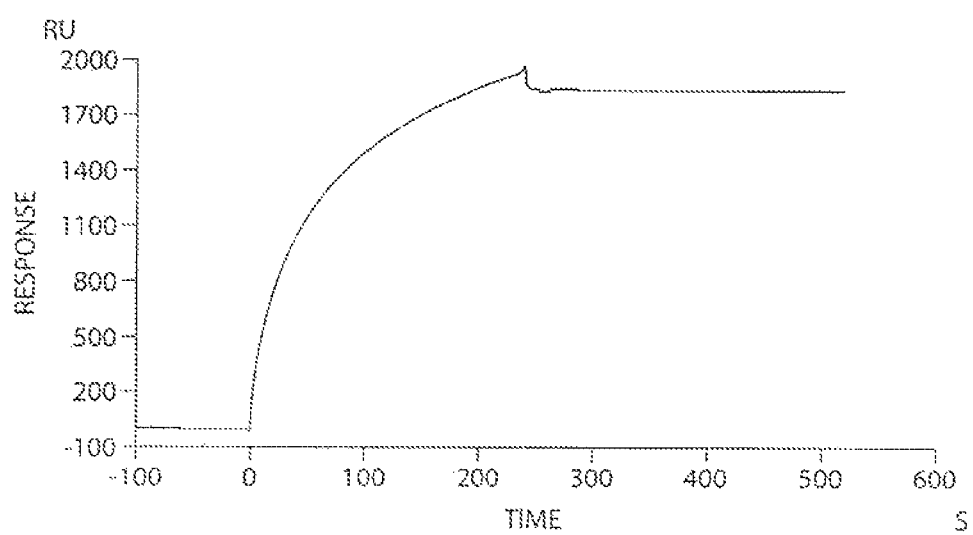
FIG. 4 Binding of Caronte to GDF-11. The tracing shows that Caronte binds to GDF-11 on a BiaCore chip. GDF-11 was immobilized on a BiaCore CMS chip using standard amine coupling procedure. Trace: Caronte (200 μg/ml; R&D Systems) was injected on the GDF-11 coupled chip.

GDF-11 is a close homolog of myostatin that regulates neurological processes. GDF-11 was immobilized on a Bia-Core CM5 chip using standard amine coupling procedure. Trace: Caronte (200 μg/ml; R&D Systems) was injected on the GDF-11 coupled chip. The tracing in FIG. 4 shows binding of Caronte to GDF-11.

Example 3

Caronte and Human Cerberus Inhibit GDF-11 and Myostatin-Mediated Signaling

Figure 5:
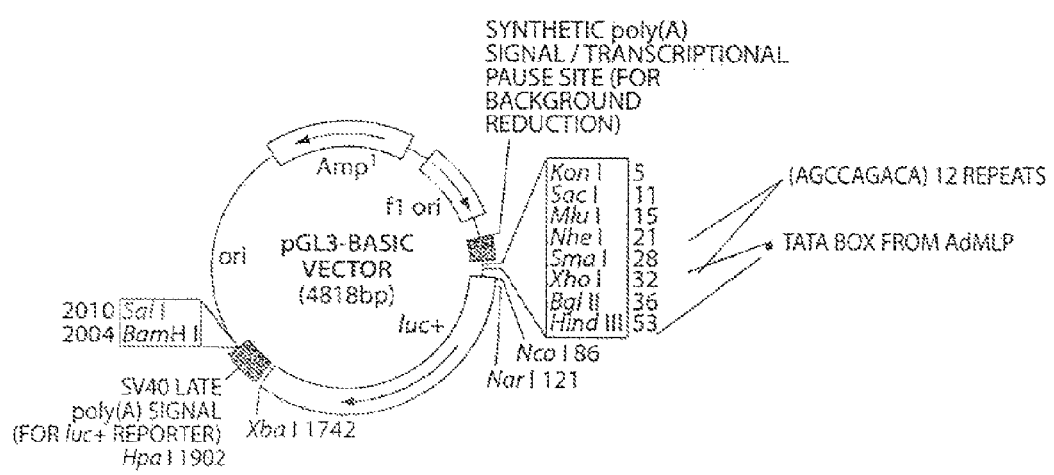
FIG. 5 A-204 Reporter Gene Assay. The figure shows the Reporter vector: pGL3(CAGA)12 (described in Dennler et al, 1998, EMBO 17: 3091-3100.) The CAGA12 motif is present in TGF-Beta responsive genes (PAI-1 gene), so this vector is of general use for factors signaling through Smad2 and 3.

An A-204 Reporter Gene Assay was used to evaluate the effects of Caronte and Cerberus on signaling by GDF-11, myostatin and Activin A. Cell line: Human Rhabdomyosarcoma (derived from muscle). Reporter vector: pGL3(CAGA) 12 (Described in Dennler et al, 1998, EMBO 17: 3091-3100.) See FIG. 5. The CAGA12 motif is present in TGF-Beta responsive genes (PAI-1 gene), so this vector is of general use for factors signaling through Smad2 and 3.

Day 1: Split A-204 cells into 48-well plate.

Day 2: A-204 cells transfected with 10 ug pGL3(CAGA)12 or pGL3(CAGA)12(10 ug)+pRLCMV (1 ug) and Fugene.

Day 3: Add factors (diluted into medium+0.1% BSA) Inhibitors need to be preincubated with Factors for 1 hr before adding to cells. 6 hrs later, cells rinsed with PBS, and lyse cells.

This is followed by a Luciferase assay. In the absence of any inhibitors, Activin A showed 10 fold stimulation of reporter gene expression and an ED50~2 ng/ml. GDF-8: ED50: ~5 ng/ml, 15 fold stimulation. GDF-11: 16 fold stimulation, ED50: ~1.5 ng/ml.

Figure 6:
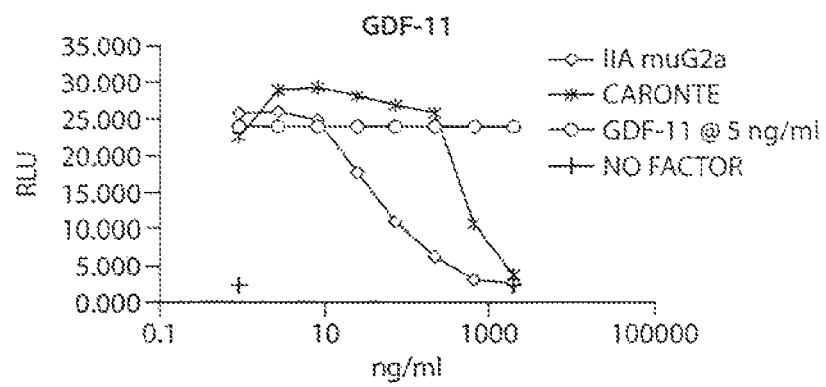
FIG. 6 Caronte inhibits GDF-11 signaling in the A-204 Reporter Gene Assay. An ActRIIA-Fc ("IIA muG2a") fusion also inhibits GDF-11 signaling.
Figure 7:
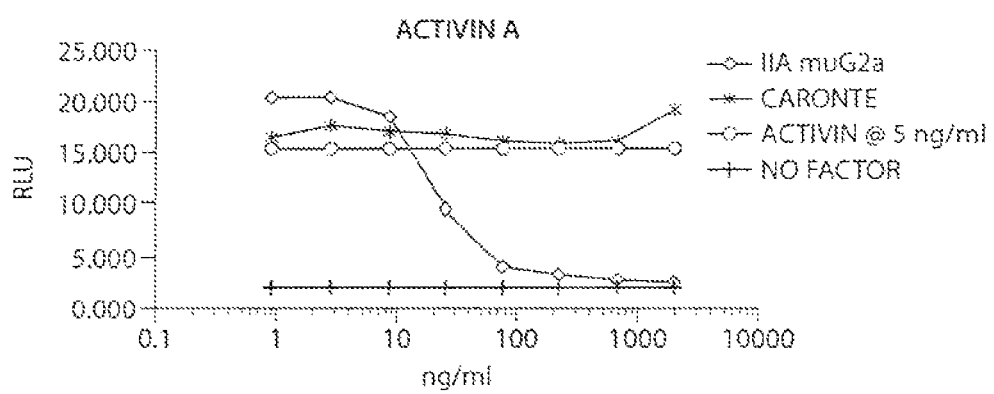
FIG. 7 Caronte does not inhibit Activin A in the A-204 Reporter Gene Assay. An ActRIIA-Fc fusion ("IIA muG2a"), as expected, does inhibit Activin A signaling.
Figure 8:
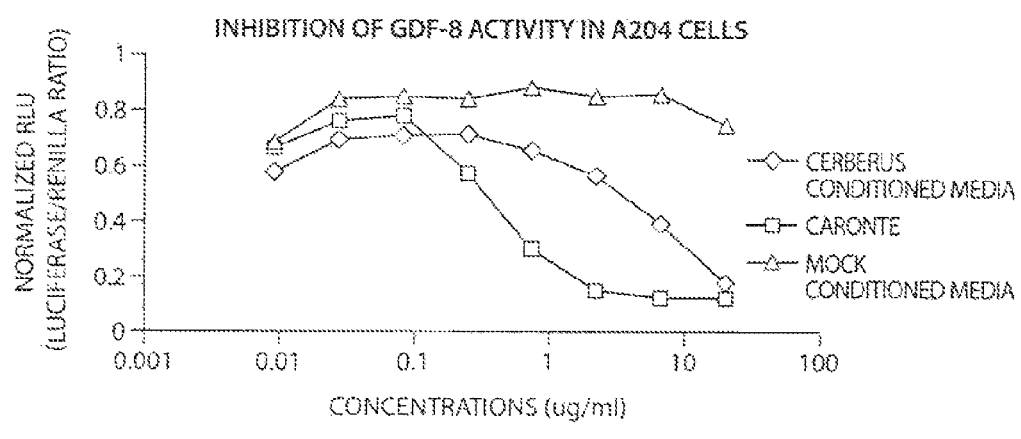
FIG. 8 Cerberus and Caronte both inhibit GDF-8 signaling in the A-204 Reporter Gene Assay.

As shown in FIG. 6, Caronte inhibits GDF-11 signaling in the A-204 Reporter Gene Assay. An ActRIIA-Fc ("IIA muG2a") fusion also inhibits GDF-11 signaling. As shown in FIG. 7, Caronte does not inhibit Activin A in the A-204 Reporter Gene Assay. An ActRIIA-Fc fusion ("IIA muG2a"), as expected, does inhibit Activin A signaling. Thus, Caronte is a selective inhibitor of GDF-11/myostatin while not affecting Activin A signaling. This type of selectivity suggests that Caronte, Cerberus and Coco will have relatively few side effects when used as a therapeutic. As expected, Cerberus behaved much like Caronte, and inhibited myostatin signaling. See FIG. 8. Similar experiments were conducted to test the binding of human Cerberus and Coco to Activin A, and these experiments confirm that these molecules do not bind to Activin A.

Example 4

Sources of Human Coco Protein

Full-length and N-terminally truncated forms of human Coco were cloned into a human CMV derived expression vector, either with or without a C-terminal fusion to an Fc portion of IgG1 (both human and murine IgG1 Fc fusions were produced). These constructs were transiently transfected in HEK293 cells using polyethylenimine (PEI). After culturing, cells were harvested and conditioned media was collected for purification.

The following construct was made, and a murine Fc fusion was made also, and used in the assays presented herein:

```
Human Coco, full length, Fc (TGGG linker (SEQ ID NO: 27) and mFc)
                                                     (SEQ ID NO: 22)
MLLGQLSTLL CLLSGALPTG SGRPEPQSPR PQSWAAANQT WALGPGALPP LVPASALGSW

KAFLGLQKAR QLGMGRLQRG QDEVAAVTLP LNPQEVIQGM CKAVPFVQVF SRPGCSAIRL

RNHLCFGHCS SLYIPGSDPT PLVLCNSCMP ARKRWAPVVL WCLTGSSASR RRVKISTMLI

EGCHCSPKA  TGGGTHTCPP CPAPELLGGP SVFLFPPKPK DTLMISRTPE VTCVVVDVSH

EDPEVKFNWY VDGVEVHNAK TKPREEQYNS TYRVVSVLTV LHQDWLNGKE YKCKVSNKAL

PVPIEKTISK AKGQPREPQV YTLPPSREEM TKNQVSLTCL VKGFYPSDIA VEWESNGQPE

NNYKTTPPVL DSDGSFFLYS KLTVDKSRWQ QGNVFSCSVM HEALHNHYTQ KSLSLSPGK

Human Coco, short form, Fc (TGGG (SEQ ID NO: 27) linker and mFc)
                                                     (SEQ ID NO: 23)
LNPQEVIQGM CKAVPFVQVF SRPGCSAIRL RNHLCFGHCS SLYIPGSDPT PLVLCNSCMP

ARKRWAPVVL WCLTGSSASR RRVKISTMLI EGCHCSPKA  TGGGTHTCPP CPAPELLGGP

SVFLFPPKPK DTLMISRTPE VTCVVVDVSH EDPEVKFNWY VDGVEVHNAK TKPREEQYNS

TYRVVSVLTV LHQDWLNGKE YKCKVSNKAL PVPIEKTISK AKGQPREPQV YTLPPSREEM

TKNQVSLTCL VKGFYPSDIA VEWESNGQPE NNYKTTPPVL DSDGSFFLYS KLTVDKSRWQ

QGNVFSCSVM HEALHNHYTQ KSLSLSPGK
```

Three different leader sequences were considered:

```
(i) Honey bee mellitin (HBML):
                                                     (SEQ ID NO: 24)
MKFLVNVALVFMVVYISYIYA (ii) Tissue Plasminogen Activator (TPA):
                                                     (SEQ ID NO: 25)
MDAMKRGLCCVLLLCGAVFVSP (iii) Native:
                                                     (SEQ ID NO: 26)
MLLGQLSTLL CLLSGALPTG S.
```

Heterologous or native leader sequences may be fused anywhere in the first 30 amino acids, and particularly N-terminal to any of amino acids 16-23.

Example 5

Human Coco Inhibits GDF-11 Signaling

Conditioned medium from cells expressing human Coco-mFc was tested for effects on A-204 reporter gene expression in the presence of GDF-11. The experiment is analogous to that described in Example 3.

Figure 9:
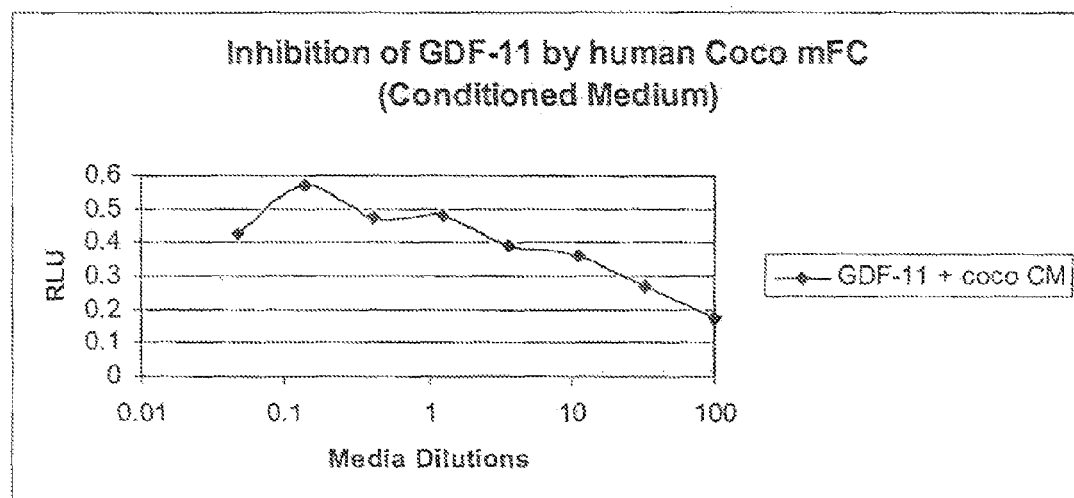
FIG. 9 Human Coco-Fc inhibits GDF-11 signaling in a cell based assay. Conditioned medium from cells expressing human Coco-mFc was tested for its effects on A-204 reporter gene expression in the presence of GDF-11.

As shown in FIG. 9, conditioned medium containing Coco-mFc inhibits GDF-11 signaling in the A-204 Reporter Gene Assay, much like Cerberus. Similar experiments showed that Coco-mFc inhibits Nodal signaling.

Example 6

Human Cerberus-Fc is Degraded in Human Serum

Figure 10:
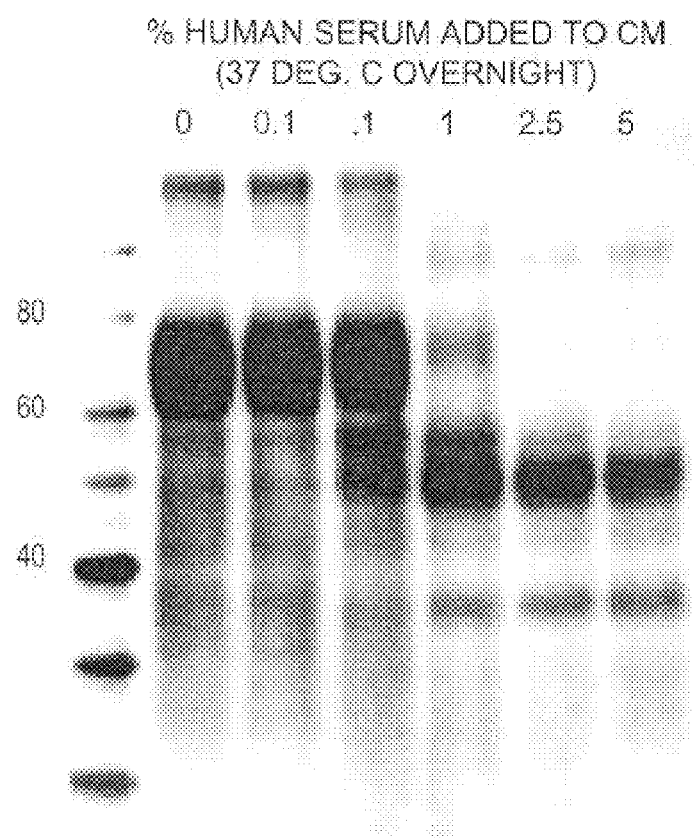
FIG. 10 Human Cerberus-Fc is degraded in human serum. Conditioned medium from cells expressing human Cerberus-Fc was incubated overnight at 37 deg. C. with varying amounts of human serum (percentages of serum added are shown at top), and resolved by SDS-PAGE. Cerberus was detected by Western blot with a primary antibody: biotinylated polyclonal anti-cerberus, and a secondary antibody: avidin-HRP. The left lane is molecular weight standards. The major band, at roughly 70 kD is Cerberus-Fc, which is completely degraded when incubated with 5% human serum.

The stability of Cerberus polypeptides in the presence of serum was evaluated. Conditioned medium from cells expressing human full-length Cerberus-Fc was incubated overnight at 37° C. with varying amounts of human serum (percentages of serum added are shown at top), and resolved by SDS-PAGE. Western blot (FIG. 10) showed that Cerberus was completely degraded when incubated with 5% human serum.

N-terminal sequencing of cleavage fragments revealed that proteolysis occurred at the following sites (cleavage shown by ^):

38 NQR^ELP 43 (SEQ ID NO: 30)
138 MFR^KTP 143 (SEQ ID NO: 31)
207 SHC^LPA 212 (SEQ ID NO: 32)

Example 7

Serum Stable Human Cerberus and Coco Polypeptides

To produce serum-stable Cerberus polypeptides, a variety of mutations may be introduced at cleavage sites and the surrounding sequences. In short forms of Cerberus, only the L212 cleavage site remains (amino acid numbering is with reference to the full length, native Cerberus sequence, SEQ ID NO: 5), and so a mutation of any, some or all of the amino acids in the sequence SHCLPA (SEQ ID NO: 32) may be altered to eliminate this cleavage site. Generally, mutations will be to small, uncharged groups, such as alanine or serine. Mutations of C211 and/or L212 to serine or alanine are particularly desirable. In addition, or in the alternative, an N-linked glycosylation site may be introduced at a position within the range of amino acids 202-222. An N-linked glycosylation site may also be introduced at a position that is expected to be proximal to the 212 position in the three-dimensional structure of the protein. Similar mutations may be made at each of the other sites 38 NQR^ELP 43 (SEQ ID NO: 30) and 138 MFR^KTP 143 (SEQ ID NO: 31), depending on the length of the Cerberus molecule to be employed. A particularly desirable mutation with respect to the 38 NQR^ELP 43 (SEQ ID NO: 30) cleavage site is an R to S/T mutation to make the sequence 38 NQ(S/T)ELP 43 (SEQ ID NO: 33), simultaneously eliminating the cleavage site and introducing an N-linked glycosylation site. Additionally, experiments have shown that products cleaved at E41 and K141 retain myostatin binding activity. Accordingly, N-terminally truncated forms of Cerberus, beginning at E41 or K141 will be resistant to cleavage at these sites and retain activity. The activity of the short form suggests that a minimal myostatin binding domain in Cerberus is the cysteine knot, located at amino acids 162-241 of SEQ ID NO:5.

Cerberus constructs with one or more of the alterations (shown in brackets below; e.g., "[R(T)]" means that an arginine normally at the position may be replaced with a threonine) will have N-linked glycosylation sites that will block cleavage and are expected to confer improved pharmacokinetic properties. The constructs below may be expressed, for example, with a tPA leader sequence and an Fc sequence.

It is expected that Coco will behave in a manner similar to Cerberus, however, the two likely cleavage sites in Coco occur within the cysteine knot domain at the sequences: 150 PAR^KRW 155 (SEQ ID NO: 35) and 168 SRR^RVK 173 (SEQ ID NO: 36) Amino acids in these positions may be altered to eliminate the cleavage, with alanine and serine being preferred amino acids. In addition, or in the alternative, an N-linked glycosylation site may be introduced at or near either of these positions. The activity of the short form of Cerberus suggests that a minimal myostatin binding domain of Coco is the cysteine knot, located at amino acids 101-185 of SEQ ID NO: 3.

Coco constructs with one or more of the alterations (shown in brackets below) will have N-linked glycosylation sites that will block cleavage and are expected to confer improved pharmacokinetic properties. The constructs below may be expressed, for example, with a tPA leader sequence and an Fc sequence.

```
                                                (SEQ ID NO: 37)
GRPEPQSPRPQSWAAANQTWALGPGALPPLVPASALGSWKAFLGLQKARQLGMG[R (N)]L[Q(T)]RGQDEVAAVTLPLNPQEVIQGMCKAVPFVQVFSRPGCSAIRLRNHLCFG

HCSSLYIPGSDPTPLVLCNSCMPA[R(N)]K[R(T)]WAPVVLWCLTGSSASR[R(N)][R(A)]

[V(S)]KISTMLIEGCHCSPKA
```

Example 8

Cysteine Variants of Cerberus and Coco

In some proteins, odd numbers of cysteine residues result in a free sulfhydryl group that may cause protein aggregation or otherwise interfere with protein production. Both native Coco and native Cerberus have odd numbers of cystein residues. In order to improve the expression of Cerberus, variants with fewer cysteine residues were generated, as well as variants with changes in proximity to one or more of the cysteines. Relative to SEQ ID NO: 5, the following variants were generated:
C176G;
C206G;
C223G;
N222D.

Each of these proteins were expressible and retained binding to GDF11, indicating that the biochemical activity of these proteins remained intact. Similar specific variants may be made with respect to Coco (relative to SEQ ID NO: 3):
C115G;
C145G;
C162G.

Therefore, the disclosure provides Cerberus and Coco variants in which one or more cysteine residues are deleted or replaced. If replaced, the replacement amino acid may be any of the other 19 canonical amino acids, although G, A, S and T are preferred.

```
                                                (SEQ ID NO: 34)
TRHQDGRQNQSSLSPVLLPRNQ[R(T)]ELPTGNHEEAEEKPDLFVAVPHLVATSPAGE

GQRQREKMLSRFGRFWKKPEREMHPSRDSDSEPFPPGTQSLIQPIDGMKMEKSPLRE

EAKKFWHHFMF[R(N)]KTPASQGVILPIKSHEVHWETCRTVPFSQTITHEGCEKVVVQ

NNLCFGKCGSVHFPGAAQHSHTSCSHCLPAKFTTMHLPLNCTELSSVIKVVMLVEEC

QCKVKTEHEDGHILH[A(N)]GSQDSFIP[G(N)]VSATG
```

EQUIVALENTS

A skilled artisan will recognize, or be able to ascertain using no more than routine experimentation, many equivalents to the specific embodiments of the invention described herein. Such equivalents are intended to be encompassed by the following claims.

The invention claimed is:

1. A method for inhibiting myostatin signal transduction in an animal, comprising: administering to an animal in need thereof a pharmaceutical preparation comprising an effective amount of a myostatin antagonist that is a fusion protein comprising the myostatin binding domain of Coco and an immunoglobulin Fc domain, wherein the myostatin binding domain of Coco comprises the amino acid sequence of SEQ ID NO: 15 or a variant thereof, and wherein said pharmaceutical preparation is substantially free of pyrogenic materials so as to be suitable for injection as a human or veterinary therapeutic.

2. The method of claim 1, wherein the animal has a pathologic condition, which is characterized, at least in part, by an abnormal amount, development or metabolic activity of muscle or adipose tissue in an animal.

3. The method of claim 1, wherein the animal has a wasting disorder.

4. The method of claim 3, wherein the wasting disorder is selected from cachexia, anorexia, Duchenne muscular dystrophy (DMD) syndrome, Becker's muscular dystrophy (BMD) syndrome, acquired immune deficiency syndrome (AIDS) wasting syndrome, age-related wasting, muscular dystrophies, and neuromuscular diseases.

5. The method of claim 1, wherein the animal has a metabolic disorder.

6. The method of claim 5, wherein the metabolic disorder is obesity or type II diabetes.

7. The method of claim 1, wherein the fusion protein has diminished potency for binding BMP-4 relative to a corresponding wild-type Coco polypeptide.

8. The method of claim 1, wherein the fusion protein binds to and neutralizes one or both of nodal and myostatin.

9. The method of claim 1, wherein the fusion protein binds myostatin with a $K_D$ of 1 µM of less.

10. The method of claim 1, wherein the fusion protein comprises an additional polypeptide portion that enhances one or more of in vivo stability, in vivo half life, uptake, tissue localization or distribution, formation of protein complexes, and/or purification.

11. The method of claim 10, wherein the additional polypeptide portion enhances purification of the fusion protein.

12. The method of claim 11, wherein the additional polypeptide portion is an epitope tag, a FLAG tag, a polyhistidine sequence, or as a GST fusion.

13. The method of claim 1, wherein the fusion protein comprises one or more modified amino acid residues, such as a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

14. The method of claim 1, wherein the fusion protein does not inhibit Activin A signaling in an A204 Reporter Gene Assay.

* * * * *